(12) United States Patent
Hennig et al.

(10) Patent No.: US 9,814,391 B2
(45) Date of Patent: Nov. 14, 2017

(54) INTRA-EXTRA ORAL SHOCK-SENSING AND INDICATING SYSTEMS AND OTHER SHOCK-SENSING AND INDICATING SYSTEMS

(71) Applicants: Don B. Hennig, Gales Creek, OR (US); Jeffry L. VanElverdinghe, Dallas, OR (US); Joseph P. Curtin, Portland, OR (US)

(72) Inventors: Don B. Hennig, Gales Creek, OR (US); Jeffry L. VanElverdinghe, Dallas, OR (US); Joseph P. Curtin, Portland, OR (US)

( * ) Notice: Subject to any disclaimer, the term of this patent is extended or adjusted under 35 U.S.C. 154(b) by 428 days.

(21) Appl. No.: 14/255,363

(22) Filed: Apr. 17, 2014

(65) Prior Publication Data
US 2014/0288432 A1     Sep. 25, 2014

Related U.S. Application Data

(63) Continuation of application No. 13/038,726, filed on Mar. 2, 2011, now Pat. No. 8,739,599, which is a
(Continued)

(51) Int. Cl.
*A61C 5/14*     (2006.01)
*A61C 19/04*    (2006.01)
(Continued)

(52) U.S. Cl.
CPC .......... *A61B 5/0053* (2013.01); *A63B 71/085* (2013.01); *A61C 19/04* (2013.01);
(Continued)

(58) Field of Classification Search
CPC ................ A61C 19/04; A63B 71/85
(Continued)

(56) References Cited

U.S. PATENT DOCUMENTS

| 257,038 A | 4/1882 | McMann |
| 1,060,220 A | 4/1913 | White |

(Continued)

FOREIGN PATENT DOCUMENTS

| WO | 2011091347 A2 | 7/2011 |
| WO | 2011091355 A2 | 7/2011 |

OTHER PUBLICATIONS

Concussion Monitoring "Intelligent Mouthguard" Project, Brain-Pad Blog, posted on Sep. 17, 2010, downloaded from http://webcache.googleusercontent.com/search?q=cache:M93BRGq-D0IJ . . . on Sep. 27, 2010, 5 pages.
(Continued)

*Primary Examiner* — Harshad R Patel
*Assistant Examiner* — Jamel Williams
(74) *Attorney, Agent, or Firm* — Joseph P. Curtin, L.L.C.

(57) ABSTRACT

A mouth guard comprises a base member configured to fit inside the mouth of a user, and at least one shock-sensing and indicating device coupled to the base member. In one exemplary embodiment, the shock-sensing and indicating device is a passive shock-sensing and indicating device that detects a shock substantially along a selected axis with respect to the base member. In another exemplary embodiment, the at least one shock-sensing and indicating device detects a shock substantially along a plurality of selected axes with respect to the base member, each selected axis being substantially orthogonal from another selected axis. The shock-sensing and indicating devices can be configured to detect different levels of shock. In one exemplary embodiment, the shock-sensing and indicating device comprises a multi-component chemical-reaction system, such as a chemi-luminescent reaction system.

4 Claims, 22 Drawing Sheets

Related U.S. Application Data continuation-in-part of application No. 12/831,860, filed on Jul. 7, 2010, now Pat. No. 8,104,324.

(60) Provisional application No. 61/309,818, filed on Mar. 2, 2010, provisional application No. 61/320,724, filed on Apr. 3, 2010, provisional application No. 61/380,480, filed on Sep. 7, 2010, provisional application No. 61/382,881, filed on Sep. 14, 2010, provisional application No. 61/412,062, filed on Nov. 10, 2010.

(51) Int. Cl.
*A61B 5/00* (2006.01)
*A63B 71/08* (2006.01)
*A63B 71/06* (2006.01)
*A63B 71/10* (2006.01)

(52) U.S. Cl.
CPC ........... *A63B 71/0619* (2013.01); *A63B 71/10* (2013.01); *A63B 2220/40* (2013.01); *A63B 2220/80* (2013.01); *A63B 2220/833* (2013.01)

(58) Field of Classification Search
USPC .............................................. 73/12.01, 12.09
See application file for complete search history.

(56) References Cited

U.S. PATENT DOCUMENTS

| | | |
|---|---|---|
| 1,117,928 A | 11/1914 | Thurmond |
| 1,323,832 A | 12/1919 | Chige |
| 1,461,209 A | 7/1923 | Bridges |
| 1,470,888 A | 10/1923 | Smedley |
| 1,487,392 A | 3/1924 | Lee |
| 1,505,978 A | 8/1924 | Stetson |
| 1,674,336 A | 6/1928 | King |
| 2,118,980 A | 5/1938 | Montgomery et al. |
| 2,250,275 A | 7/1941 | Riddell |
| 2,257,709 A | 9/1941 | Anderson |
| 2,296,335 A | 9/1942 | Brady |
| 2,423,005 A | 6/1947 | Chaiken |
| 2,521,039 A | 9/1950 | Carpenter |
| 2,590,118 A | 3/1952 | Oddo, Jr. |
| 2,616,081 A | 11/1952 | Weaver et al. |
| 2,630,117 A | 3/1953 | Coleman |
| 2,643,652 A | 6/1953 | Cathcart |
| 2,659,366 A | 11/1953 | Savarese |
| 2,678,043 A | 5/1954 | Stark |
| 2,669,988 A | 9/1954 | Carpenter |
| 2,694,397 A | 11/1954 | Herms |
| 2,702,032 A | 2/1955 | Freedland |
| 2,708,931 A | 5/1955 | Freedland |
| 2,750,941 A | 6/1956 | Cathcart |
| 2,825,297 A | 3/1958 | Harrison |
| 2,833,278 A | 5/1958 | Ross |
| 2,847,003 A | 8/1958 | Helmer et al. |
| 2,850,740 A | 9/1958 | Adams |
| 2,867,811 A | 1/1959 | Jones |
| 2,867,812 A | 1/1959 | Roth et al. |
| 2,898,596 A | 8/1959 | Keen |
| 2,908,911 A | 10/1959 | Sowle |
| 2,933,811 A | 4/1960 | Lifton |
| 2,966,908 A | 1/1961 | Cathcart et al. |
| 2,985,883 A | 5/1961 | Marietta |
| 2,986,739 A | 6/1961 | Rozzi, Sr |
| 3,009,158 A | 11/1961 | Comeau et al. |
| 3,016,052 A | 1/1962 | Zubren |
| 3,020,875 A | 2/1962 | Browning |
| 3,021,813 A | 2/1962 | Rips |
| 3,041,623 A | 7/1962 | Glahe |
| 3,058,462 A | 10/1962 | Greenblum |
| 3,073,300 A | 1/1963 | Berghash |
| 3,082,765 A | 3/1963 | Helmer |
| 3,087,166 A | 4/1963 | Howard |
| 3,106,716 A | 10/1963 | Beebe |
| 3,107,667 A | 10/1963 | Moore |
| 3,113,318 A | 12/1963 | Marietta |
| 3,124,129 A | 3/1964 | Grossberg |
| 3,126,002 A | 3/1964 | Owens |
| 3,139,624 A | 7/1964 | Humphrey |
| 3,149,606 A | 9/1964 | Falkner |
| 3,166,761 A | 1/1965 | Strohm |
| 3,167,783 A | 2/1965 | Wolfe |
| 3,174,155 A | 3/1965 | Pitman |
| 3,186,004 A | 6/1965 | Carlini |
| 3,187,342 A | 6/1965 | Aileo |
| 3,189,917 A | 6/1965 | Sims |
| 3,203,417 A | 8/1965 | Helmer |
| 3,207,153 A | 9/1965 | Goldstein |
| 3,216,023 A | 11/1965 | Morgan |
| 3,223,085 A | 12/1965 | Gores et al. |
| 3,230,544 A | 1/1966 | Mager |
| 3,239,842 A | 3/1966 | Marchello |
| 3,242,500 A | 3/1966 | Derr |
| 3,247,844 A | 4/1966 | Berghash |
| 3,274,612 A | 9/1966 | Merriam |
| 3,310,811 A | 3/1967 | Iacono, Jr. |
| 3,312,218 A | 4/1967 | Jacobs |
| 3,314,077 A | 4/1967 | Marchello |
| 3,319,626 A | 5/1967 | Lindsay |
| 3,323,134 A | 6/1967 | Swyers |
| 3,339,207 A | 9/1967 | Perry |
| 3,373,443 A | 3/1968 | Marietta |
| 3,380,294 A | 4/1968 | Redmond |
| 3,407,809 A | 10/1968 | Ross |
| 3,411,501 A | 11/1968 | Greenberg |
| D212,848 S | 12/1968 | Westlund |
| 3,416,527 A | 12/1968 | Hoef |
| 3,448,738 A | 6/1969 | Berghash |
| 3,457,916 A | 7/1969 | Wolicki |
| 3,462,763 A | 8/1969 | Schneider et al. |
| D215,685 S | 10/1969 | Helmer |
| 3,478,365 A | 11/1969 | Varga |
| 3,485,242 A | 12/1969 | Greenberg |
| 3,496,936 A | 2/1970 | Gores |
| 3,505,995 A | 4/1970 | Greenberg |
| 3,518,988 A | 7/1970 | Gores |
| 3,532,091 A | 10/1970 | Lerman |
| 3,548,410 A | 12/1970 | Parker |
| 3,591,863 A | 7/1971 | Rickard |
| 3,608,089 A | 9/1971 | Abatelli |
| 3,619,813 A | 11/1971 | Marchello |
| 3,629,864 A | 12/1971 | Latina |
| 3,682,164 A | 8/1972 | Miller |
| 3,692,025 A | 9/1972 | Greenberg |
| 3,707,722 A | 12/1972 | Itoh |
| 3,729,744 A | 5/1973 | Rappleyea |
| D228,048 S | 8/1973 | Miller |
| 3,751,728 A | 8/1973 | Thompkins |
| 3,768,465 A | 10/1973 | Helmer |
| 3,787,895 A | 1/1974 | Belvedere |
| 3,806,951 A | 4/1974 | Halteman |
| 3,815,152 A | 6/1974 | Bednarczuk et al. |
| 3,818,509 A | 6/1974 | Romo et al. |
| 3,864,832 A | 2/1975 | Carlson |
| 3,873,997 A | 4/1975 | Gooding |
| 3,889,296 A | 6/1975 | Martin |
| 3,897,597 A | 8/1975 | Kasper |
| 3,897,598 A | 8/1975 | Bednarczuk et al. |
| 3,916,446 A | 11/1975 | Gooding |
| 3,916,527 A | 11/1975 | Linkow |
| 3,924,638 A | 12/1975 | Mann |
| 3,925,821 A | 12/1975 | Lewicki |
| 3,943,924 A | 3/1976 | Kallestad et al. |
| 4,004,450 A | 1/1977 | Yakshin et al. |
| 4,021,858 A | 5/1977 | Neeld et al. |
| 4,023,396 A | 5/1977 | Yakshin et al. |
| 4,030,339 A | 6/1977 | Yakshin et al. |
| 4,030,493 A | 6/1977 | Walters et al. |
| 4,044,400 A | 8/1977 | Lewicki et al. |
| 4,044,762 A | 8/1977 | Jacobs |
| 4,051,556 A | 10/1977 | Davenport et al. |
| 4,055,842 A | 10/1977 | Yakshin et al. |

(56) References Cited

U.S. PATENT DOCUMENTS

| | | | |
|---|---|---|---|
| 4,062,068 A | 12/1977 | Davenport et al. |
| 4,063,552 A | 12/1977 | Going et al. |
| 4,068,613 A | 1/1978 | Rubey |
| 4,103,640 A | 8/1978 | Feder |
| 4,114,614 A | 9/1978 | Kesling |
| 4,125,085 A | 11/1978 | Rubey |
| 3,513,838 A | 5/1979 | Foderick et al. |
| 4,161,874 A | 7/1979 | Specker et al. |
| 4,185,817 A | 1/1980 | Peterson |
| 4,211,008 A | 7/1980 | Lerman |
| 4,239,014 A | 12/1980 | Rubey |
| 4,271,537 A | 6/1981 | Bowlus et al. |
| 4,330,272 A | 5/1982 | Bergersen |
| 4,335,472 A | 6/1982 | Rappleyea |
| 4,337,765 A | 7/1982 | Zimmerman |
| 4,346,205 A | 8/1982 | Hiles |
| 4,348,178 A | 9/1982 | Kurz |
| 4,361,106 A | 11/1982 | Eklof |
| 4,370,129 A | 1/1983 | Huge |
| 4,376,628 A | 3/1983 | Aardse |
| 4,398,306 A | 8/1983 | Gooding |
| 4,446,576 A | 5/1984 | Hisataka |
| 4,452,066 A | 6/1984 | Klochko et al. |
| 4,457,708 A | 7/1984 | Dufour |
| 4,470,302 A | 9/1984 | Carte |
| 4,490,112 A | 12/1984 | Tanaka et al. |
| 4,492,121 A | 1/1985 | Lehto |
| 4,495,945 A | 1/1985 | Liegner |
| 4,519,386 A | 5/1985 | Sullivan |
| 4,519,867 A | 5/1985 | Rubey |
| 4,568,280 A | 2/1986 | Ahlin |
| 4,591,341 A | 5/1986 | Andrews |
| 4,640,273 A | 2/1987 | Greene et al. |
| 4,646,368 A | 3/1987 | Infusino et al. |
| 4,651,356 A | 3/1987 | Zide |
| 4,663,785 A * | 5/1987 | Comparetto ............ A42B 3/00 2/413 |
| 4,671,766 A | 6/1987 | Norton |
| 4,672,959 A | 6/1987 | May et al. |
| 4,691,556 A | 9/1987 | Mellander et al. |
| 4,692,947 A | 9/1987 | Black et al. |
| 4,727,867 A | 3/1988 | Knoderer |
| 4,741,054 A | 5/1988 | Mattes |
| 4,755,139 A | 7/1988 | Abbatte et al. |
| 4,763,275 A * | 8/1988 | Carlin ................... A42B 3/046 273/148 R |
| 4,763,791 A | 8/1988 | Halverson et al. |
| 4,765,324 A | 8/1988 | Lake, Jr. |
| 4,791,941 A | 12/1988 | Schaefer |
| 4,793,803 A | 12/1988 | Martz |
| 4,799,500 A | 1/1989 | Newbury |
| 4,810,192 A | 3/1989 | Williams |
| 4,829,812 A | 5/1989 | Parks et al. |
| 4,848,365 A | 7/1989 | Guarlotti et al. |
| 4,867,147 A | 9/1989 | Davis |
| 4,873,867 A | 10/1989 | McPherson et al. |
| 4,944,947 A | 7/1990 | Newman |
| 4,955,393 A | 9/1990 | Adell |
| 4,977,905 A | 12/1990 | Kittelsen et al. |
| 4,979,516 A | 12/1990 | Abraham, II |
| 4,989,462 A | 2/1991 | Davis et al. |
| 5,031,611 A | 7/1991 | Moles |
| 5,031,638 A | 7/1991 | Castaldi |
| 5,063,940 A | 11/1991 | Adell et al. |
| 5,076,785 A | 12/1991 | Tsai |
| 5,078,153 A | 1/1992 | Nordlander et al. |
| 5,082,007 A | 1/1992 | Adell |
| 5,092,346 A | 3/1992 | Hays et al. |
| 5,103,838 A | 4/1992 | Yousif |
| 5,112,225 A | 5/1992 | Diesso |
| 5,117,816 A | 6/1992 | Shapiro et al. |
| D328,494 S | 8/1992 | Schwendeman et al. |
| 5,152,301 A | 10/1992 | Kittelsen et al. |
| 5,154,609 A | 10/1992 | George |
| 5,165,424 A | 11/1992 | Silverman |
| 5,174,284 A | 12/1992 | Jackson |
| 5,194,003 A | 3/1993 | Garay et al. |
| 5,194,004 A | 3/1993 | Bergersen |
| 5,203,351 A | 4/1993 | Adell |
| 5,234,005 A | 8/1993 | Kittelsen et al. |
| 5,235,991 A | 8/1993 | Minneman |
| 5,242,830 A | 9/1993 | Argy et al. |
| 5,245,706 A | 9/1993 | Moschetti et al. |
| 5,259,762 A | 11/1993 | Farrell |
| 5,269,252 A | 12/1993 | Nagai |
| 5,277,202 A | 1/1994 | Hays |
| 5,277,203 A | 1/1994 | Hays |
| D343,928 S | 2/1994 | Kittelsen |
| 5,293,880 A | 3/1994 | Levitt |
| 5,297,960 A | 3/1994 | Burns |
| 5,299,936 A | 4/1994 | Ueno |
| 5,313,960 A | 5/1994 | Tomasi |
| 5,316,474 A | 5/1994 | Robertson |
| 5,320,114 A | 6/1994 | Kittelsen et al. |
| 5,323,787 A | 6/1994 | Pratt |
| 5,326,945 A | 7/1994 | Gotoh et al. |
| 5,328,362 A | 7/1994 | Watson et al. |
| 5,336,086 A | 8/1994 | Simmen et al. |
| 5,339,832 A | 8/1994 | Kittelsen et al. |
| 5,343,569 A * | 9/1994 | Asare ................... A42B 3/0433 2/411 |
| 5,347,660 A | 9/1994 | Zide et al. |
| 5,353,810 A | 10/1994 | Kittelsen et al. |
| 5,365,946 A | 11/1994 | McMillan |
| 5,385,155 A | 1/1995 | Kittelsen et al. |
| 5,386,821 A | 2/1995 | Poterack |
| D356,188 S | 3/1995 | Kittelsen |
| 5,401,234 A | 3/1995 | Libin |
| 5,406,963 A | 4/1995 | Adell |
| 5,447,168 A | 9/1995 | Bancroft |
| 5,460,527 A | 10/1995 | Kittelsen et al. |
| 5,462,066 A | 10/1995 | Snyder |
| 5,469,865 A | 11/1995 | Minneman |
| 5,490,411 A | 2/1996 | Hogan |
| 5,490,520 A | 2/1996 | Schaefer et al. |
| 5,511,562 A | 4/1996 | Hancock |
| 5,513,656 A | 5/1996 | Boyd, Sr. |
| 5,533,524 A | 7/1996 | Minneman |
| 5,539,935 A | 7/1996 | Rush, III |
| D373,421 S | 9/1996 | Brown |
| 5,551,279 A | 9/1996 | Quick |
| 5,566,684 A | 10/1996 | Wagner |
| 5,584,687 A | 12/1996 | Sullivan et al. |
| 5,590,643 A | 1/1997 | Flam |
| 5,592,951 A | 1/1997 | Castagnaro et al. |
| 5,621,922 A * | 4/1997 | Rush, III ............... A42B 3/046 2/422 |
| 5,624,257 A | 4/1997 | Farrell |
| 5,636,379 A | 6/1997 | Williams |
| 5,646,216 A | 7/1997 | Watson et al. |
| D382,965 S | 8/1997 | Wagner |
| 5,655,227 A | 8/1997 | Sundberg et al. |
| 5,666,973 A | 9/1997 | Walter |
| 5,692,523 A | 12/1997 | Croll et al. |
| 5,718,243 A | 2/1998 | Weatherford et al. |
| 5,718,575 A | 2/1998 | Cross, III |
| 5,724,681 A | 3/1998 | Sykes |
| 5,730,599 A | 3/1998 | Pak |
| 5,732,414 A | 3/1998 | Monica |
| 5,741,970 A | 4/1998 | Rubin |
| 5,746,221 A | 5/1998 | Jones et al. |
| 5,770,792 A | 6/1998 | Nakada et al. |
| D397,442 S | 8/1998 | Kittelsen |
| 5,794,274 A | 8/1998 | Kraemer |
| 5,799,337 A | 9/1998 | Brown |
| 5,816,255 A | 10/1998 | Fishman et al. |
| 5,819,744 A | 10/1998 | Stoyka, Jr. |
| 5,823,193 A | 10/1998 | Singer et al. |
| 5,823,194 A | 10/1998 | Lampert |
| 5,826,281 A | 10/1998 | Rush, III |
| 5,826,581 A | 10/1998 | Yoshida |
| 5,836,761 A | 11/1998 | Belvedere et al. |
| 5,865,619 A | 2/1999 | Cross, III et al. |
| 5,873,365 A | 2/1999 | Brown |

(56) References Cited

U.S. PATENT DOCUMENTS

| | | |
|---|---|---|
| D406,405 S | 3/1999 | Yoshida |
| 5,879,155 A | 3/1999 | Kittelsen |
| 5,884,628 A | 3/1999 | Hilsen |
| D408,919 S | 4/1999 | Cooley |
| 5,893,174 A | 4/1999 | Primeau |
| 5,915,385 A | 6/1999 | Hakimi |
| 5,915,538 A | 6/1999 | Basson et al. |
| 5,921,240 A | 7/1999 | Gall |
| 5,931,164 A | 8/1999 | Kiely et al. |
| 5,946,735 A | 9/1999 | Bayes |
| 5,947,918 A | 9/1999 | Jones et al. |
| 5,950,624 A | 9/1999 | Hart |
| 5,970,981 A | 10/1999 | Ochel |
| 5,978,972 A | 11/1999 | Stewart et al. |
| 6,012,919 A | 1/2000 | Cross, III et al. |
| 6,036,487 A | 3/2000 | Westerman |
| 6,039,046 A | 3/2000 | Swartz et al. |
| 6,065,158 A * | 5/2000 | Rush, III .............. A42B 3/067 2/412 |
| 6,068,475 A | 5/2000 | Stoyka, Jr. |
| 6,073,272 A | 6/2000 | Ball |
| 6,081,932 A | 7/2000 | Kraemer |
| 6,082,363 A | 7/2000 | Washburn |
| 6,089,864 A | 7/2000 | Buckner et al. |
| 6,092,524 A | 7/2000 | Barnes, Sr. |
| 6,098,627 A | 8/2000 | Kellner et al. |
| 6,109,266 A | 8/2000 | Turchetti |
| D434,501 S | 11/2000 | Redhage |
| 6,152,138 A | 11/2000 | Brown et al. |
| 6,189,156 B1 | 2/2001 | Loiars |
| 6,200,133 B1 | 3/2001 | Kittelsen |
| 6,222,524 B1 | 4/2001 | Salem et al. |
| 6,237,601 B1 | 5/2001 | Kittelsen et al. |
| 6,257,239 B1 | 7/2001 | Kittelsen et al. |
| 6,298,483 B1 | 10/2001 | Schiebl et al. |
| 6,299,441 B1 | 10/2001 | Novak |
| 6,301,718 B1 * | 10/2001 | Rigal .................... A42B 3/046 2/411 |
| D452,011 S | 12/2001 | Redhage |
| 6,324,701 B1 | 12/2001 | Alexander |
| 6,332,226 B1 | 12/2001 | Rush, III |
| 6,371,758 B1 | 4/2002 | Kittelsen |
| 6,381,757 B2 | 5/2002 | Rush, III |
| 6,393,892 B1 | 5/2002 | Ohbayashi et al. |
| 6,415,794 B1 | 7/2002 | Kittelsen et al. |
| 6,481,024 B1 | 11/2002 | Grant |
| 6,491,036 B2 | 12/2002 | Cook |
| 6,491,037 B1 | 12/2002 | Mortenson |
| 6,494,210 B1 | 12/2002 | Mams |
| 6,499,139 B1 | 12/2002 | Brown et al. |
| 6,505,626 B2 | 1/2003 | Kittelsen et al. |
| 6,505,627 B2 | 1/2003 | Kittelsen et al. |
| 6,505,628 B2 | 1/2003 | Kittelsen et al. |
| 6,508,251 B2 | 1/2003 | Kittelsen et al. |
| 6,510,853 B1 | 1/2003 | Kittelsen et al. |
| 6,532,602 B2 | 3/2003 | Watters et al. |
| D473,976 S | 4/2003 | Wilkens |
| 6,539,943 B1 | 4/2003 | Kittelsen et al. |
| 6,553,996 B2 | 4/2003 | Kittelsen et al. |
| 6,581,604 B2 | 6/2003 | Cook |
| 6,584,978 B1 | 7/2003 | Brett et al. |
| 6,588,430 B2 | 7/2003 | Kittelsen et al. |
| 6,598,605 B1 | 7/2003 | Kittelsen et al. |
| 6,602,633 B1 | 8/2003 | Ohbayashi et al. |
| 6,613,001 B1 | 9/2003 | Dworkin |
| 6,626,180 B1 | 9/2003 | Kittelsen et al. |
| 6,633,454 B1 | 10/2003 | Martin et al. |
| 6,675,806 B2 | 1/2004 | Kittelsen et al. |
| 6,675,807 B2 | 1/2004 | Kittelsen et al. |
| 6,691,710 B2 | 2/2004 | Kittelsen et al. |
| 6,698,272 B1 | 3/2004 | Almirante |
| 6,711,751 B1 | 3/2004 | Muskovitz |
| D493,578 S | 7/2004 | Manzo et al. |
| 6,769,286 B2 | 8/2004 | Biermann et al. |
| 6,782,558 B1 | 8/2004 | Keen, Sr. et al. |
| D496,154 S | 9/2004 | Herman et al. |
| D496,498 S | 9/2004 | Kittelsen et al. |
| D496,499 S | 9/2004 | Kittelsen et al. |
| 6,804,829 B2 | 10/2004 | Crye et al. |
| 6,820,623 B2 | 11/2004 | Cook |
| D500,895 S | 1/2005 | Manzo et al. |
| D500,897 S | 1/2005 | Herman et al. |
| D500,898 S | 1/2005 | Herman et al. |
| D501,062 S | 1/2005 | Herman et al. |
| 6,848,389 B1 | 2/2005 | Elsasser et al. |
| 6,854,133 B2 | 2/2005 | Lee et al. |
| 6,858,810 B2 | 2/2005 | Zerbini et al. |
| D502,787 S | 3/2005 | Liu |
| D502,995 S | 3/2005 | Cook et al. |
| D504,744 S | 5/2005 | Hidalgo et al. |
| D509,028 S | 8/2005 | Farrell |
| 6,934,971 B2 | 8/2005 | Ide et al. |
| 6,941,952 B1 * | 9/2005 | Rush, III .............. A63B 71/085 128/845 |
| D523,994 S | 6/2006 | Manzo |
| D525,749 S | 7/2006 | Manzo et al. |
| 7,069,601 B1 | 7/2006 | Jacobson |
| D526,093 S | 8/2006 | Manzo et al. |
| D526,095 S | 8/2006 | Manzo et al. |
| D527,848 S | 9/2006 | Manzo et al. |
| D529,615 S | 10/2006 | Atz |
| D530,863 S | 10/2006 | Manzo et al. |
| D532,559 S | 11/2006 | Manzo et al. |
| 7,152,253 B2 | 12/2006 | Abelman et al. |
| 7,159,442 B1 | 1/2007 | Jean |
| 7,178,175 B2 | 2/2007 | Rogers et al. |
| D537,986 S | 3/2007 | Manzo et al. |
| D537,987 S | 3/2007 | Manzo et al. |
| D539,484 S | 3/2007 | Hillman |
| 7,194,889 B1 | 3/2007 | Jean et al. |
| D541,481 S | 4/2007 | Farrell |
| 7,210,483 B1 | 5/2007 | Lesniak et al. |
| 7,216,371 B2 | 5/2007 | Wong |
| 7,246,384 B2 | 7/2007 | Bentz |
| 7,246,385 B2 | 7/2007 | Dennis et al. |
| D548,402 S | 8/2007 | Trodick |
| D548,403 S | 8/2007 | Manzo et al. |
| 7,266,988 B2 | 9/2007 | Kranz et al. |
| D554,259 S | 10/2007 | Diacopoulos et al. |
| 7,290,437 B1 | 11/2007 | Tanaka et al. |
| 7,299,804 B2 | 11/2007 | Kittelsen et al. |
| D570,549 S | 6/2008 | Essig |
| D570,724 S | 6/2008 | Kittelsen et al. |
| 7,383,728 B2 | 6/2008 | Noble et al. |
| 7,386,401 B2 | 6/2008 | Vock et al. |
| D572,430 S | 7/2008 | Wong |
| 7,404,403 B2 | 7/2008 | Farrell |
| D584,002 S | 12/2008 | Essig |
| 7,481,773 B1 | 1/2009 | Dorroh et al. |
| D586,252 S | 2/2009 | Kittelsen |
| 7,509,835 B2 | 3/2009 | Beck |
| 7,526,389 B2 * | 4/2009 | Greenwald ............ A42B 3/046 2/425 |
| D593,714 S | 6/2009 | Hirshberg |
| 7,549,423 B1 | 6/2009 | Hirshberg |
| D595,857 S | 7/2009 | Massad |
| D597,675 S | 8/2009 | Eli |
| D601,265 S | 9/2009 | Lin |
| D601,711 S | 10/2009 | Lin |
| D603,101 S | 10/2009 | Hirshberg |
| 7,607,438 B2 | 10/2009 | Pelerin |
| D611,658 S | 3/2010 | Manzo |
| D615,709 S | 5/2010 | Manzo |
| D616,152 S | 5/2010 | Manzo |
| 7,708,018 B1 | 5/2010 | Hirshberg |
| 7,770,239 B1 | 8/2010 | Goldman et al. |
| 7,775,214 B1 | 8/2010 | Lesniak et al. |
| D623,357 S | 9/2010 | Manzo |
| 7,798,149 B2 | 9/2010 | Haduong |
| D625,470 S | 10/2010 | Willems |
| D626,292 S | 10/2010 | Farrell |
| 7,810,502 B1 | 10/2010 | Nguyen et al. |
| D627,107 S | 11/2010 | Manzo et al. |
| 7,827,991 B2 | 11/2010 | Maher |

(56) References Cited

U.S. PATENT DOCUMENTS

| | | |
|---|---|---|
| 7,832,404 B2 | 11/2010 | Jansheski |
| D630,382 S | 1/2011 | Manzo et al. |
| 7,861,722 B2 | 1/2011 | Keropian |
| 7,861,724 B2 | 1/2011 | Keropian |
| 7,882,839 B2 | 2/2011 | Ambis, Jr. |
| 7,886,370 B2 | 2/2011 | Winningham |
| 7,890,193 B2 | 2/2011 | Tingey |
| D634,480 S | 3/2011 | Manzo et al. |
| 7,895,677 B1 | 3/2011 | Schiebl |
| 7,900,279 B2 | 3/2011 | Kraemer et al. |
| 7,913,695 B1 | 3/2011 | Moore et al. |
| D636,074 S | 4/2011 | Levine |
| 7,918,228 B2 | 4/2011 | Smernoff |
| 7,950,394 B2 | 5/2011 | Elkin et al. |
| 7,963,286 B2 | 6/2011 | Burdumy |
| D642,277 S | 7/2011 | Farrell |
| 7,972,024 B2 | 7/2011 | DeLeeuw |
| 7,975,701 B2 | 7/2011 | Bergersen |
| 7,987,854 B2 | 8/2011 | Arni |
| 8,006,322 B1 | 8/2011 | Schiebl |
| 8,007,277 B2 | 8/2011 | Fischer et al. |
| 8,091,148 B2 | 1/2012 | Ho |
| 8,170,242 B2 | 5/2012 | Menzel et al. |
| 8,196,226 B1 | 6/2012 | Schuh |
| 8,235,917 B2 * | 8/2012 | Joseph ............... A61B 18/1206 600/590 |
| 8,316,691 B2 | 11/2012 | Jeftic-Stojanovski et al. |
| 8,466,794 B2 | 6/2013 | Mack et al. |
| 8,537,017 B2 | 9/2013 | Mack et al. |
| 8,554,495 B2 | 10/2013 | Mack et al. |
| 8,771,149 B2 | 7/2014 | Rahman et al. |
| 2001/0004772 A1 | 6/2001 | Rush, III |
| 2002/0066454 A1 | 6/2002 | Kittelsen et al. |
| 2002/0144686 A1 | 10/2002 | Cook |
| 2002/0144687 A1 | 10/2002 | Kittelsen et al. |
| 2002/0144688 A1 | 10/2002 | Kittelsen et al. |
| 2002/0144689 A1 | 10/2002 | Kittelsen et al. |
| 2002/0144690 A1 | 10/2002 | Kittelsen et al. |
| 2002/0144691 A1 | 10/2002 | Kittelsen et al. |
| 2002/0144692 A1 | 10/2002 | Kittelsen et al. |
| 2002/0144693 A1 | 10/2002 | Kittelsen et al. |
| 2002/0144694 A1 | 10/2002 | Kittelsen et al. |
| 2002/0144695 A1 | 10/2002 | Cook |
| 2003/0040679 A1 | 2/2003 | Weber et al. |
| 2003/0075186 A1 | 4/2003 | Florman |
| 2003/0101999 A1 | 6/2003 | Kittelsen et al. |
| 2003/0126665 A1 | 7/2003 | Brown et al. |
| 2003/0154990 A1 | 8/2003 | Parker |
| 2004/0003452 A1 | 1/2004 | Scheibl |
| 2004/0025231 A1 | 2/2004 | Ide et al. |
| 2004/0040073 A1 | 3/2004 | Morrow et al. |
| 2004/0103905 A1 | 6/2004 | Farrell |
| 2004/0107970 A1 | 6/2004 | Kittelsen et al. |
| 2004/0112389 A1 | 6/2004 | Abraham |
| 2004/0244805 A1 | 12/2004 | Cook et al. |
| 2004/0250817 A1 | 12/2004 | Kittelsen et al. |
| 2005/0052724 A1 | 3/2005 | Suzuki et al. |
| 2005/0113654 A1 | 5/2005 | Weber et al. |
| 2005/0115571 A1 | 6/2005 | Jacobs |
| 2005/0177929 A1 | 8/2005 | Greenwald et al. |
| 2005/0247318 A1 | 11/2005 | Mohindra |
| 2006/0117466 A1 | 6/2006 | Abelman et al. |
| 2006/0150304 A1 | 7/2006 | Bentz |
| 2006/0162421 A1 | 7/2006 | Mess |
| 2007/0011796 A1 | 1/2007 | Manzo |
| 2007/0084471 A1 | 4/2007 | Napoli et al. |
| 2007/0089219 A1 | 4/2007 | Trainor et al. |
| 2007/0089480 A1 | 4/2007 | Beck |
| 2007/0151567 A1 | 7/2007 | Maurello |
| 2007/0151568 A1 | 7/2007 | Maurello |
| 2007/0235039 A1 | 10/2007 | Gottsch |
| 2007/0251294 A1 | 11/2007 | Tanaka et al. |
| 2008/0016605 A1 | 1/2008 | Wong |
| 2008/0028500 A1 | 2/2008 | Bentz |
| 2008/0043248 A1 | 2/2008 | Ozcan |
| 2008/0092277 A1 | 4/2008 | Kraemer et al. |
| 2009/0000377 A1 | 1/2009 | Shipps et al. |
| 2009/0114232 A1 | 5/2009 | Landi et al. |
| 2009/0122525 A1 | 5/2009 | DeLeeuw |
| 2009/0265841 A1 | 10/2009 | Ferrara |
| 2009/0307827 A1 | 12/2009 | Aspray |
| 2009/0308403 A1 | 12/2009 | Roettger et al. |
| 2010/0005571 A1 | 1/2010 | Moss et al. |
| 2010/0006109 A1 | 1/2010 | McGinnis et al. |
| 2010/0015808 A1 | 1/2010 | Ozawa |
| 2010/0024833 A1 | 2/2010 | Swann et al. |
| 2010/0051038 A1 | 3/2010 | Quigless |
| 2010/0073678 A1 | 3/2010 | Smith et al. |
| 2010/0083733 A1 | 4/2010 | Russell et al. |
| 2010/0104998 A1 | 4/2010 | Farrell et al. |
| 2010/0108078 A1 | 5/2010 | Morgan et al. |
| 2010/0129763 A1 | 5/2010 | Kuo |
| 2010/0212674 A1 | 8/2010 | Navarrette, Jr. |
| 2010/0269836 A1 | 10/2010 | Roettger et al. |
| 2010/0275930 A1 | 11/2010 | Evans |
| 2010/0288290 A1 | 11/2010 | Lee et al. |
| 2010/0318294 A1 | 12/2010 | Rosing et al. |
| 2010/0326192 A1 | 12/2010 | Petelenz et al. |
| 2010/0326451 A1 | 12/2010 | Pelerin |
| 2011/0005531 A1 | 1/2011 | Manzo |
| 2011/0009773 A1 | 1/2011 | Hower et al. |
| 2011/0017221 A1 | 1/2011 | Garner et al. |
| 2011/0030704 A1 | 2/2011 | Hanna |
| 2011/0067710 A1 | 3/2011 | Jansheski et al. |
| 2011/0067711 A1 | 3/2011 | Jansheski et al. |
| 2011/0088703 A1 | 4/2011 | Ambis, Jr. |
| 2011/0094522 A1 | 4/2011 | Weisflog |
| 2011/0100379 A1 | 5/2011 | Doctors et al. |
| 2011/0114100 A1 | 5/2011 | Alvarez et al. |
| 2011/0132380 A1 | 6/2011 | Goldsby |
| 2011/0139162 A1 | 6/2011 | Chodorow |
| 2011/0139163 A1 | 6/2011 | Hillila |
| 2011/0155146 A1 | 6/2011 | Marsh |
| 2011/0168186 A1 | 7/2011 | Halstrom |
| 2011/0174319 A1 | 7/2011 | Busciglio |
| 2011/0179851 A1 * | 7/2011 | Mack ..................... A42B 3/046 73/1.79 |
| 2011/0181418 A1 | 7/2011 | Mack et al. |
| 2011/0181419 A1 | 7/2011 | Mack et al. |
| 2011/0181420 A1 | 7/2011 | Mack et al. |
| 2011/0184319 A1 * | 7/2011 | Mack ..................... A42B 3/046 600/595 |
| 2011/0184663 A1 | 7/2011 | Mack et al. |
| 2011/0186055 A1 | 8/2011 | Makkar et al. |
| 2011/0186056 A1 | 8/2011 | Smernoff |
| 2011/0203347 A1 | 8/2011 | Hower et al. |
| 2011/0209714 A1 | 9/2011 | Makkar et al. |
| 2011/0214478 A1 | 9/2011 | Hennig et al. |
| 2011/0219852 A1 | 9/2011 | Kasten |
| 2011/0277221 A1 | 11/2011 | Ide et al. |
| 2012/0111090 A1 | 5/2012 | Hennig et al. |
| 2012/0111091 A1 | 5/2012 | Hennig et al. |
| 2012/0123225 A1 | 5/2012 | Al-Tawil |
| 2012/0210498 A1 | 8/2012 | Mack |
| 2012/0223833 A1 | 9/2012 | Thomas et al. |
| 2012/0306438 A1 | 12/2012 | Howard et al. |
| 2014/0039355 A1 | 2/2014 | Crisco, III et al. |
| 2016/0018278 A1 * | 1/2016 | Jeter, II .................. A41D 13/00 340/665 |

OTHER PUBLICATIONS

Heads Up! Concussion Detector, Aug. 1. 2010, downloaded from http://www.aip.org/dbis/stories/2010/20094.html on Sep. 27, 2010, 2 pages.

Heads Up! Concussion Detector—full report, downloaded from http://www.aip.org/dbis/stories/2010/20094_full.html of Sep. 27, 2010, 1 page.

Mouth guard acts as concussion detector, last updated Aug. 11, 2010, downloaded from http://www.cfnews13.com/article/news/2010/august/134230/Mouth-guar . . . on Sep. 27, 2010, 2 pages.

Mouth guard for concussion protection, from HealthNewsDigest.

(56) References Cited

OTHER PUBLICATIONS com, May 17, 2010, downloaded from http://healthnewsdigest.com/news/Health_Tips_620/Mouth_Guard_for_C . . . on Sep. 28, 2010, 2 pages.

New Mouth Guard Could Prevent Football Injuries, Sep. 25, 2010, downloaded from http://www.10tv.com/live/content/onnnews/stories/2010/09/25/story-intel . . . on Sep. 27, 2010, 2 pages.

Sports Dentistry Online, downloaded from http://www.sportsdentistry.com/concussion.html on Sep. 27, 2010, 3 pages.

Higgins et al., "Measurement of Impact Acceleration: Mouthpiece Accelerometer Versus Helmet Accelerometer," Journal of Athletic Training, Jan.-Mar. 2007, 42(1): 5-10, downloaded Aug. 29, 2011, 9 pages.

U.S. Appl. No. 12/831,860, Office Action dated Sep. 20, 2011, 9 pages.

\* cited by examiner

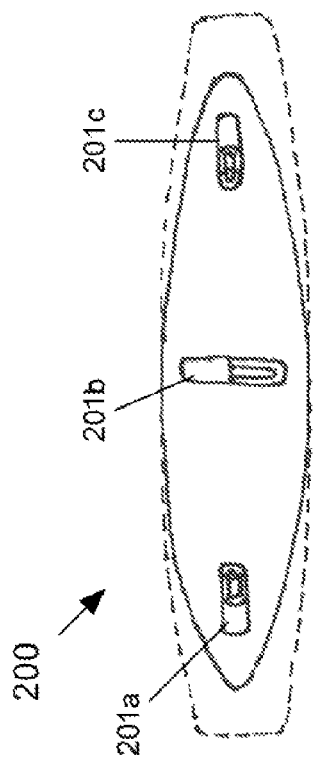
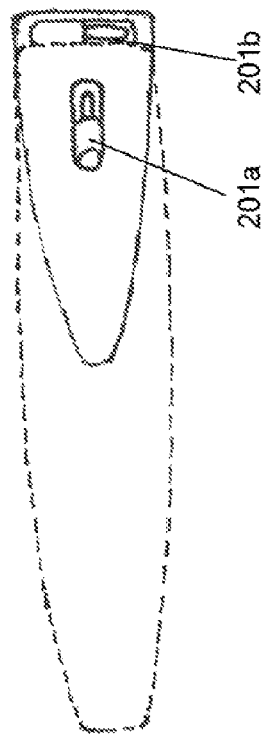
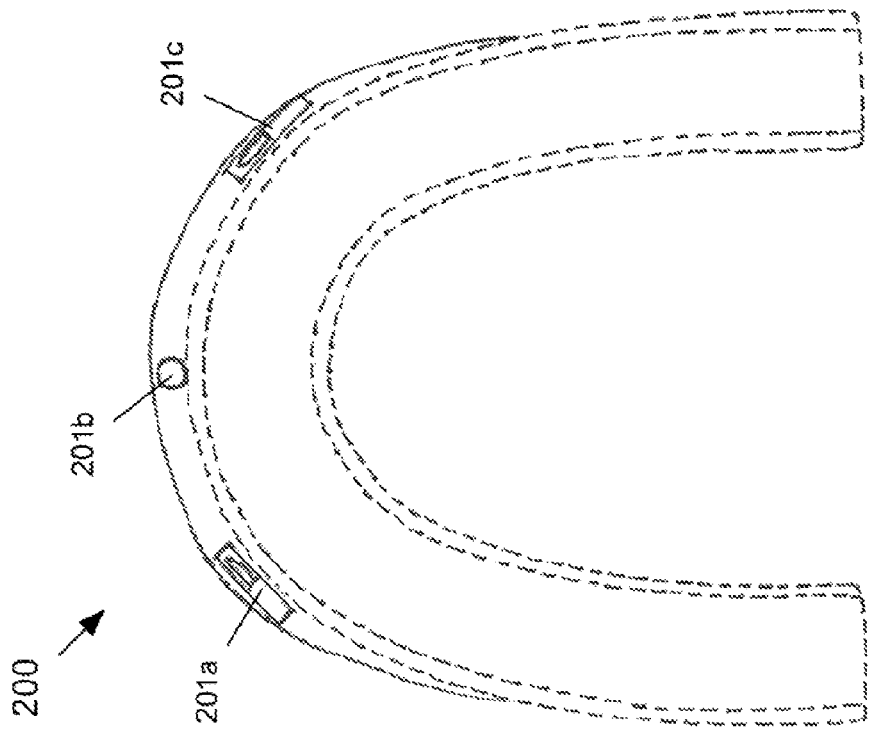

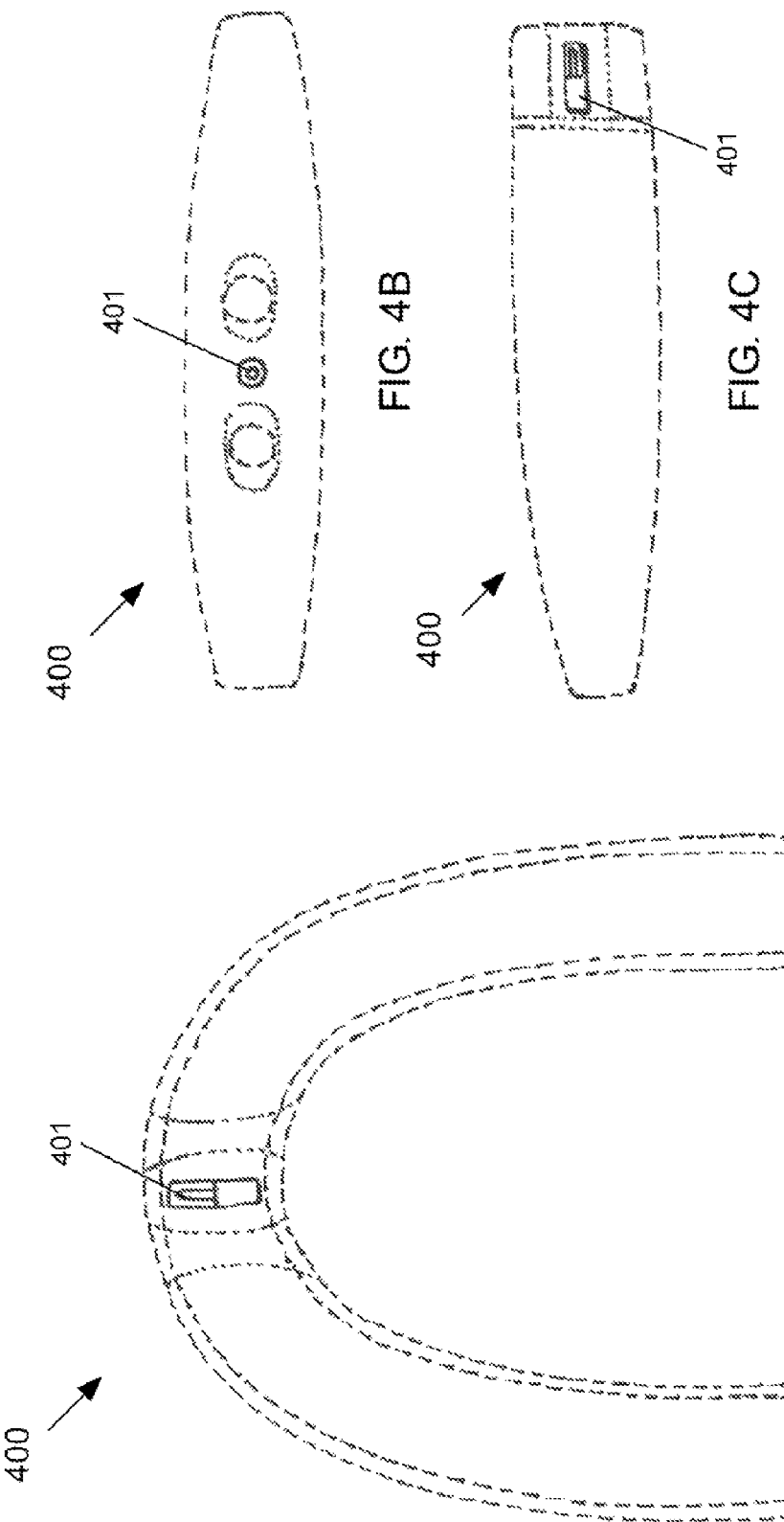

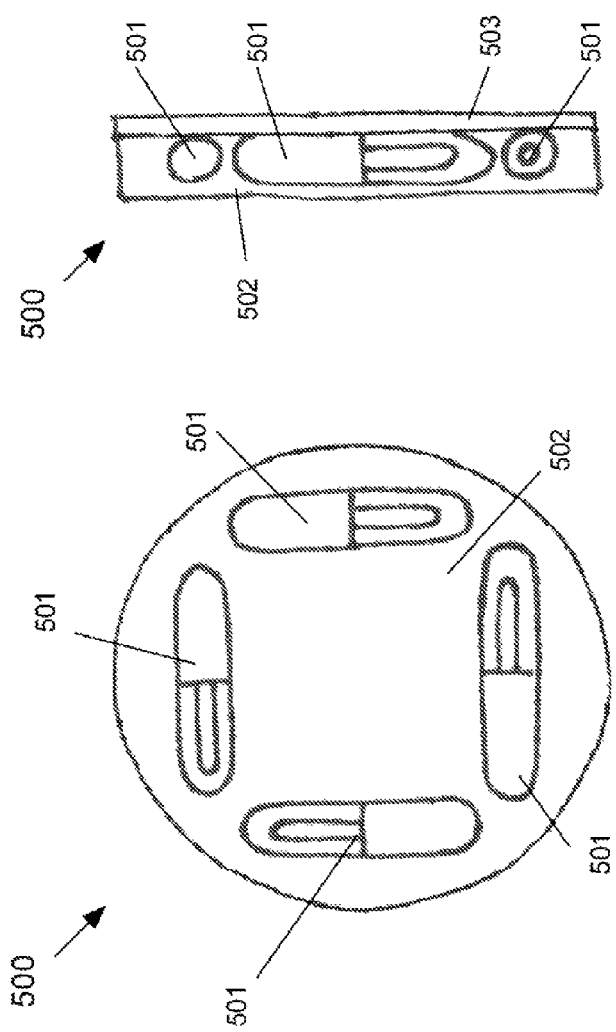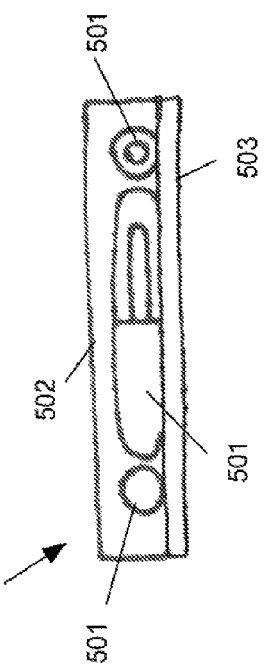
FIG. 5A
FIG. 5B
FIG. 5C

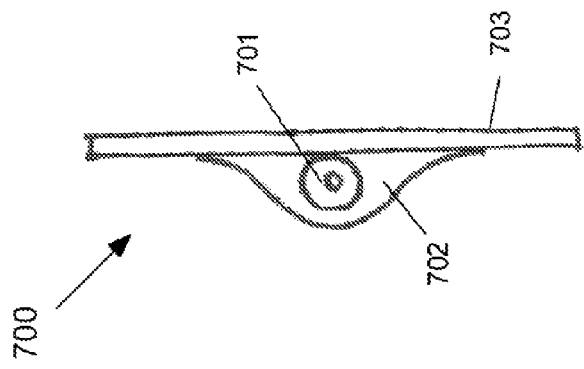
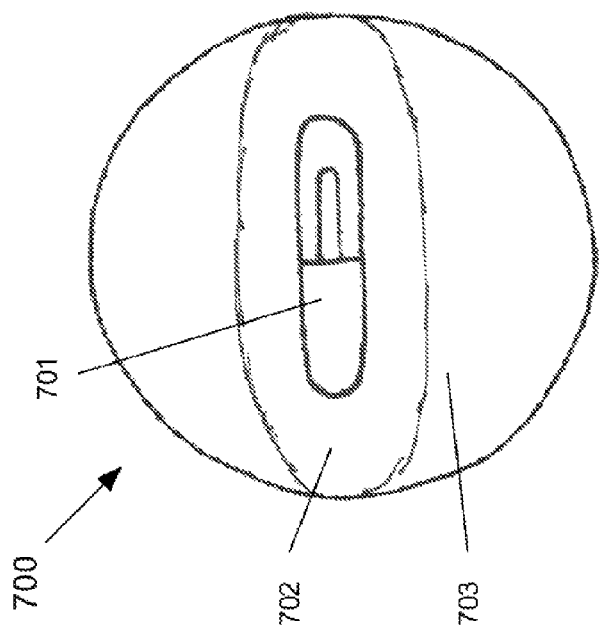
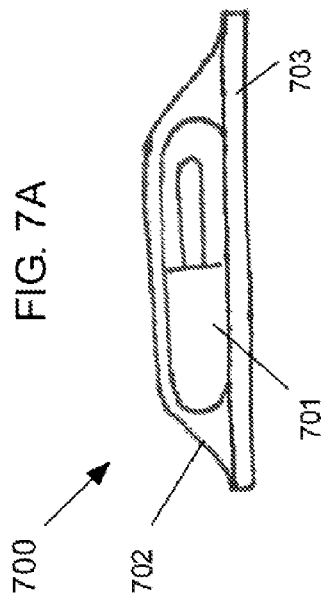
FIG. 7C
FIG. 7A
FIG. 7B

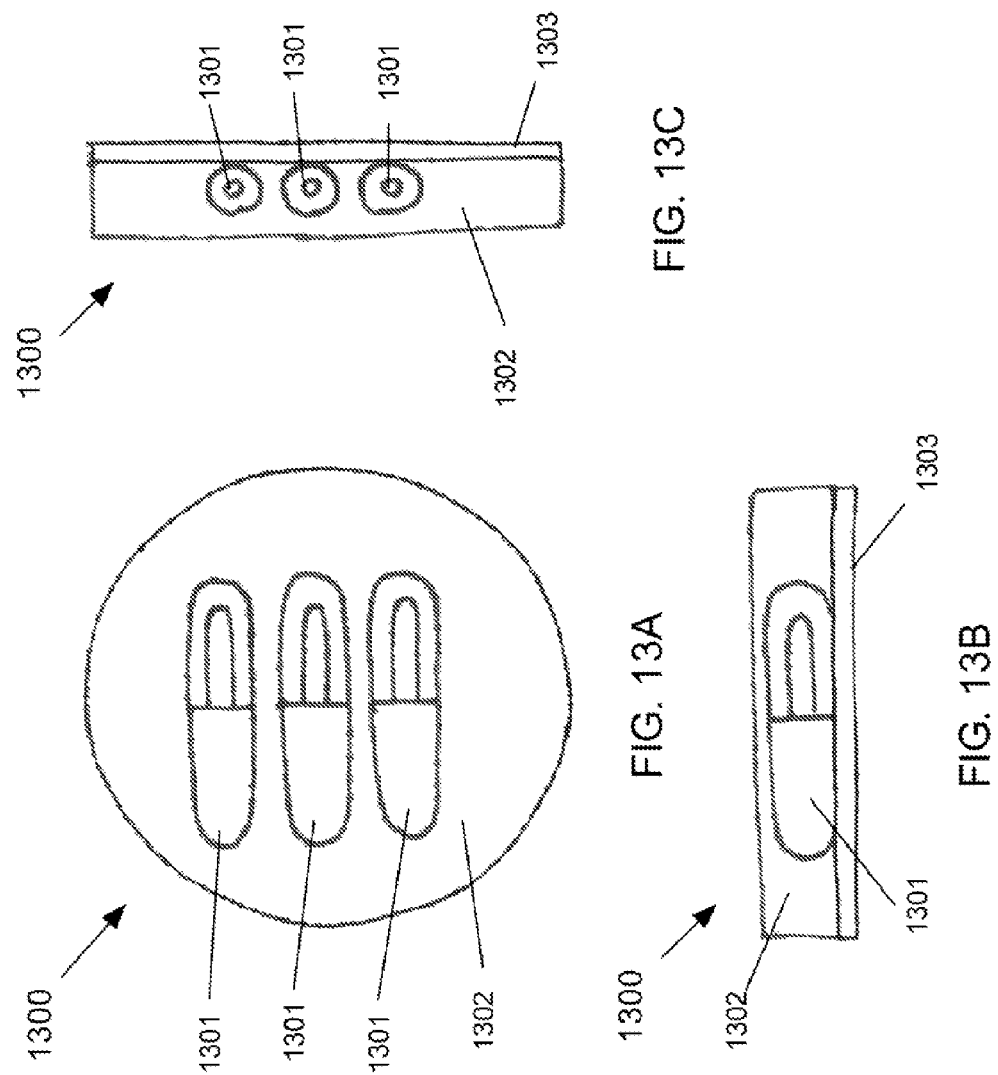

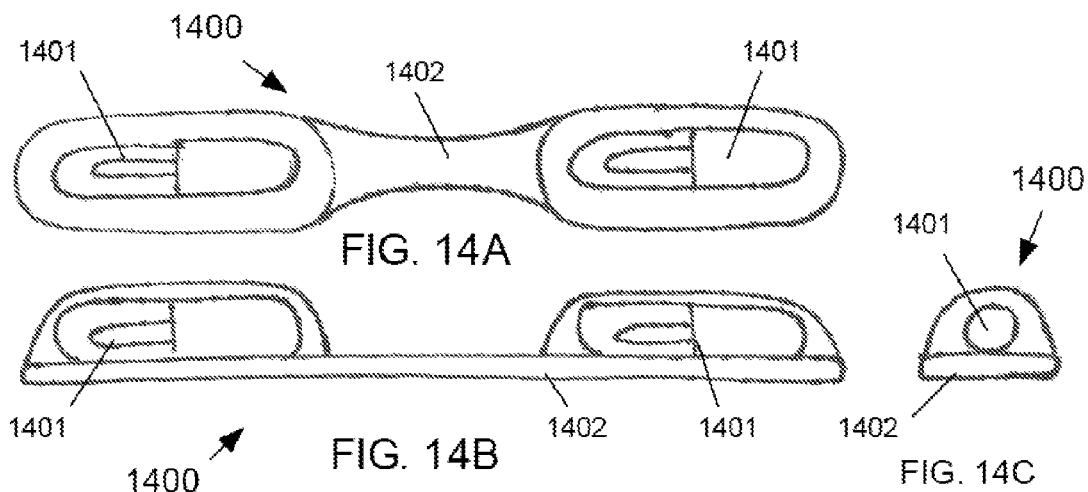
FIG. 14A
FIG. 14B
FIG. 14C
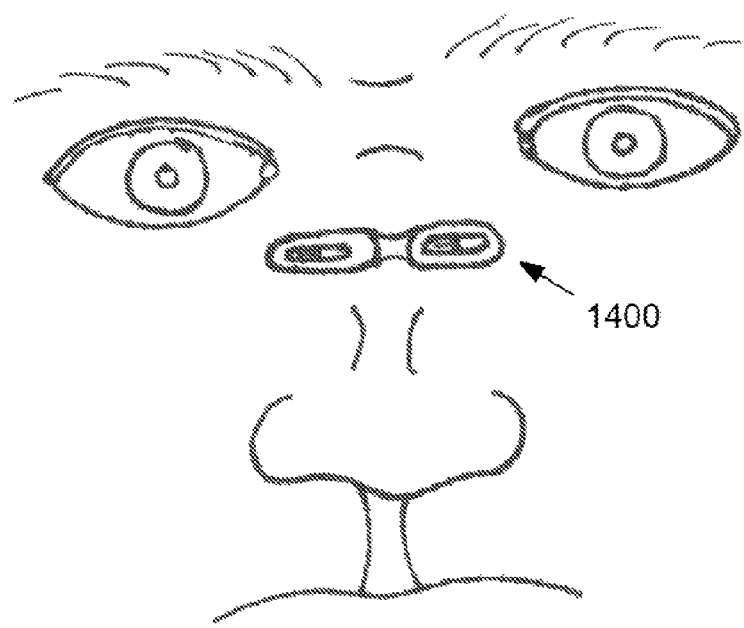
FIG. 14D

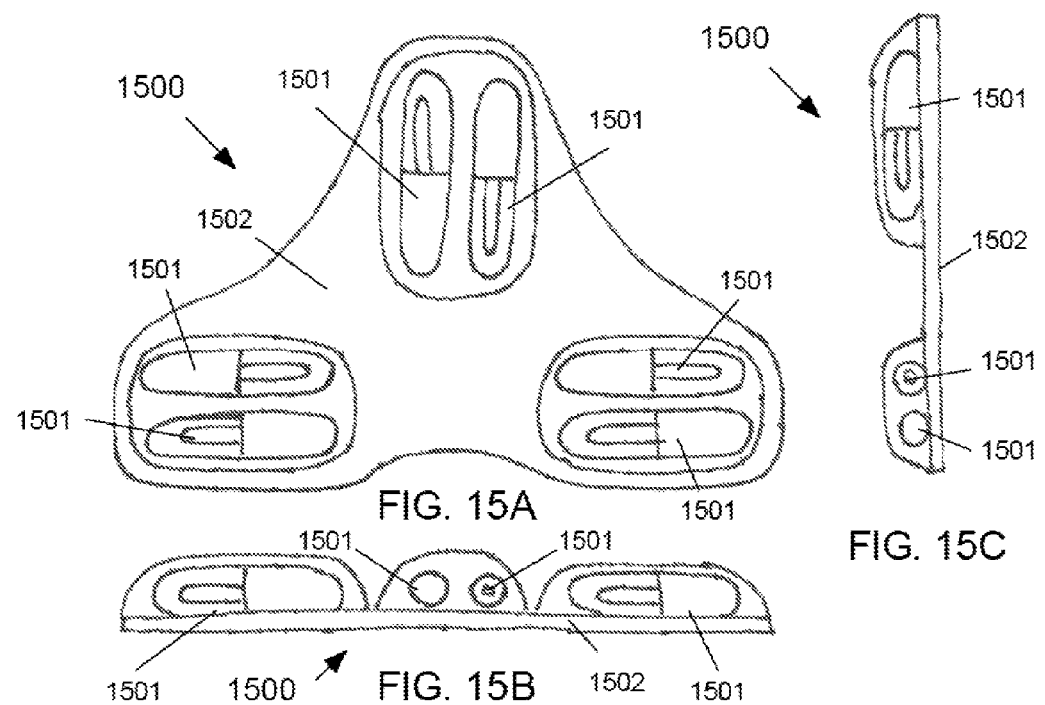
FIG. 15A
FIG. 15B
FIG. 15C
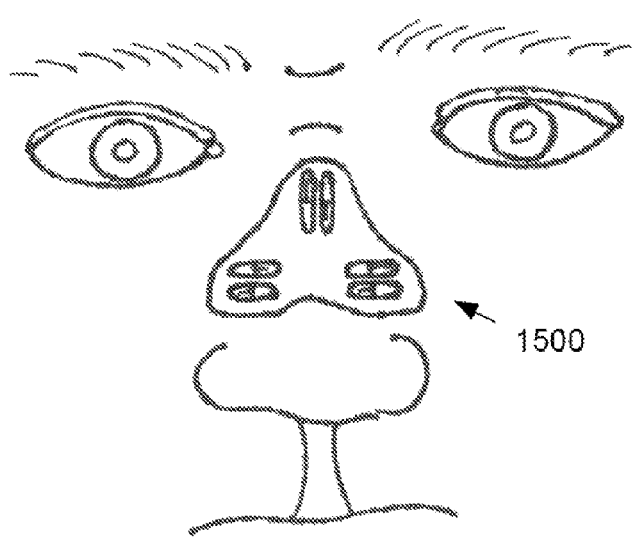
FIG. 15D

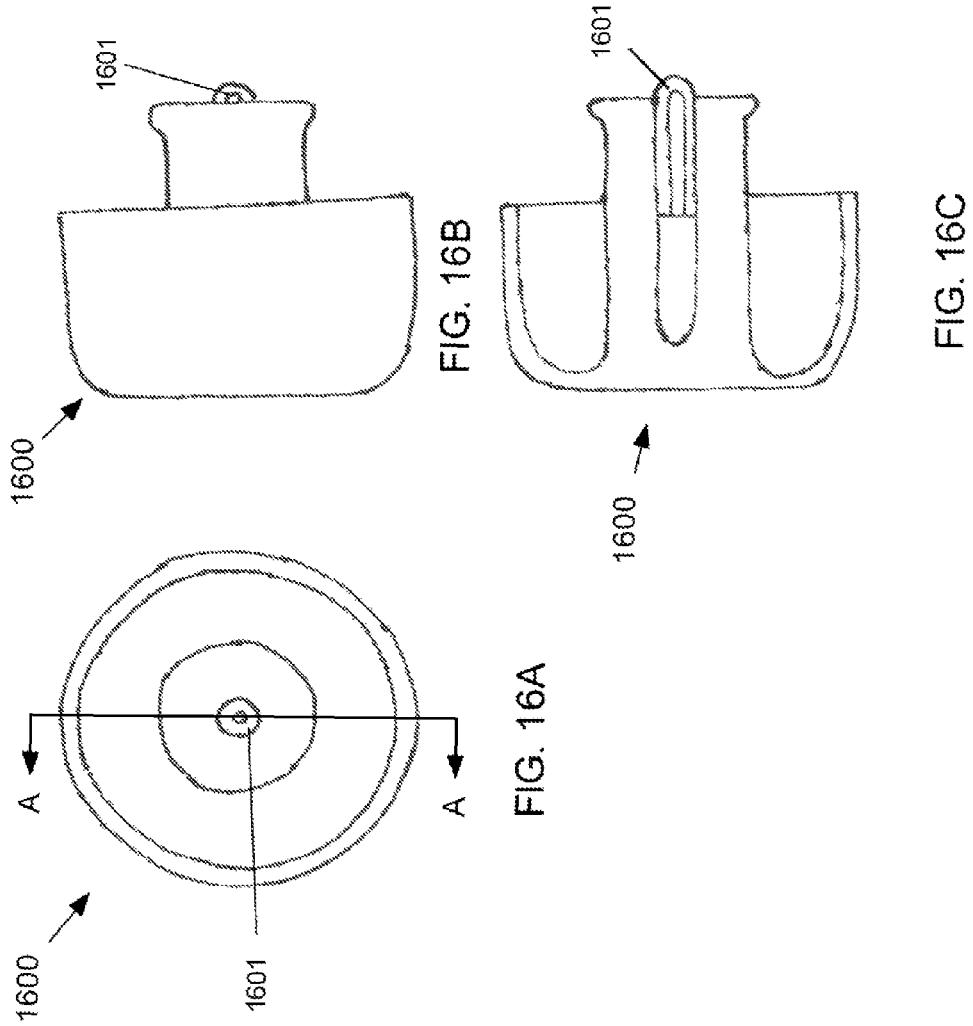

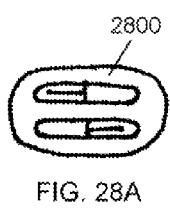
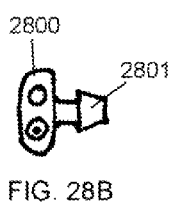
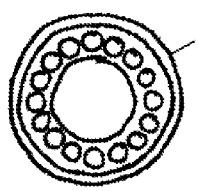
FIG. 28A  FIG. 28B  FIG. 29A
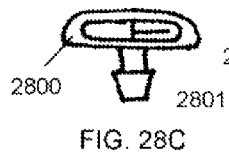
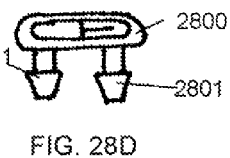
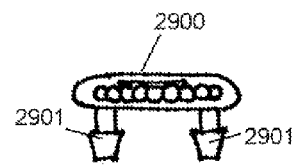
FIG. 28C  FIG. 28D  FIG. 29B  FIG. 29C
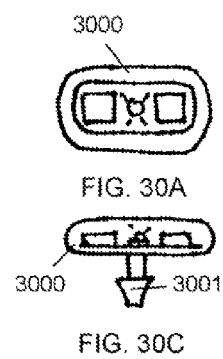
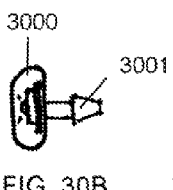
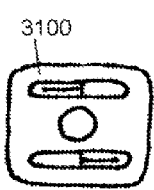
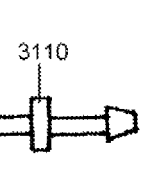
FIG. 30A  FIG. 30B  FIG. 31A  FIG. 31B  FIG. 31D
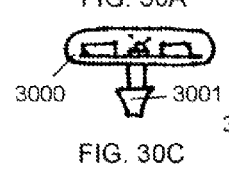
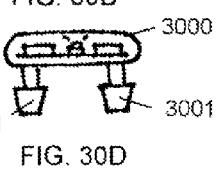
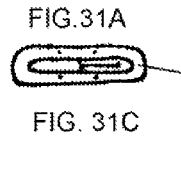
FIG. 30C  FIG. 30D  FIG. 31C
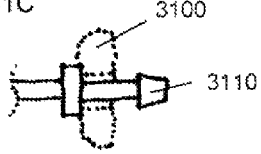
FIG. 31E

INTRA-EXTRA ORAL SHOCK-SENSING AND INDICATING SYSTEMS AND OTHER SHOCK-SENSING AND INDICATING SYSTEMS

CROSS-REFERENCES TO RELATED PATENT APPLICATIONS

The present patent application is a continuation patent application of U.S. patent application Ser. No. 13/038,726, entitled "Intra-Extra Oral Shock-Sensing And Indicating Systems And Other Shock-Sensing And Indicating Systems," invented by Don B. Hennig et al., and filed Mar. 2, 2011, now U.S. Pat. No. 8,739,599 B2, issued Jun. 3, 2014, which is a continuation-in-part patent application of and claims priority to U.S. Non-Provisional Patent Application Ser. No. 12/831,860, entitled "Intra-Extra Oral Shock-Sensing And Indicating Systems And Other Shock-Sensing And Indicating Systems," invented by Don B. Hennig et al., filed Jul. 7, 2010, now U.S. Pat. No. 8,104,324, issued Jan. 31, 2012, and the present patent application is related to and claims priority to each of U.S. Provisional Patent Application Ser. No. 61/412,062, entitled "Shock-Detecting Device," invented by Don B. Hennig et al., filed Nov. 10, 2010, U.S. Provisional Patent Application Ser. No. 61/382,881, entitled "Shock-Detecting Device," invented by Don B. Hennig et al., filed Sep. 14, 2010; U.S. Provisional Patent Application Ser. No. 61/380,480, entitled "Shock-Detecting Device," invented by Jeffry L. VanElverdinghe et al., filed Sep. 7, 2010; U.S. Provisional Patent Application Ser. No. 61/309,818, entitled "Intra-Extra Oral Shock Sensing And Indicating System (IOSSIS)," invented by Don B. Hennig, filed Mar. 2, 2010; and U.S. Provisional Patent Application Ser. No. 61/320,724, entitled "Intra-Extra Oral Shock Sensing And Indicating System (IOSSIS)," invented by Don B. Hennig et al., filed Apr. 3, 2010. The disclosures of each are incorporated by reference herein.

BACKGROUND

Shock sensing technologies incorporated into helmets or headgear does not accurately reflect shock experienced by a wearer of the helmet.

BRIEF DESCRIPTION OF THE DRAWINGS

The subject matter disclosed herein is illustrated by way of example and not by limitation in the accompanying figures in which like reference numerals indicate similar elements and in which:

FIGS. 2A-2C respectively depict top, front and side views of an exemplary embodiment of a mouth-guard device that comprises three shock-sensing and indicating devices that, in use, is positioned in the mouth of a user for sensing and recording shock experienced by the user;

FIGS. 4A-4C respectively depict top, front and side view of an exemplary embodiment of a mouth-guard device that comprises one shock-sensing and indicating device that, in use, is positioned in the mouth of a user for sensing and recording shock experienced by the user;

FIGS. 5A-5C respective depict front, right-side and bottom views of an exemplary embodiment of a shock-sensing unit comprising four passive-shock-sensing and indicating devices, such as passive-tube-type sensor/detector/indicators, that are suitable for use with the subject matter disclosed herein;

FIGS. 7A-7C respectively depict front, right-side and bottom views of an exemplary embodiment of a shock-sensing unit comprising one passive-shock-sensing device, such as a passive-tube-type sensor/detector/indicator, that are suitable for use with the subject matter disclosed herein;

FIGS. 13A-13C respectively depict front, right-side and bottom views of an exemplary embodiment of a shock-sensing unit comprising three passive-shock-sensing devices, such as passive-tube-type sensor/detector/indicators;

FIGS. 14A-14C respectively depict front, side and end views of an exemplary embodiment of a shock-sensing unit comprising two shock-sensing devices attached in a well-known manner to a substrate having an adhesive coating that is used for attaching shocking-sensing unit to the body of a user, or to a piece of equipment or clothing worn by the user.

FIG. 14D depicts the shock-sensing device depicted in FIGS. 14A-14C being worn as an adhesive nasal strip by a user;

FIGS. 15A-15C respectively depict front, side and bottom views of an exemplary embodiment of a shock-sensing unit comprising six shock-sensing devices attached in a well-known manner to a substrate having an adhesive coating that is used for attaching shocking-sensing unit to the body of a user, or to a piece of equipment or clothing worn by the user.

FIG. 15D depicts shock-sensing device depicted in FIGS. 15A-15C being worn as an adhesive nasal strip by a user;

FIGS. 16A and 16B respectively depict front and side views of an exemplary embodiment of a shock-sensing unit configured to fit into the ear of a user and comprising one shock-sensing device;

FIG. 16C is a cross-sectional view of the exemplary embodiment of the shock-sensing unit depicted in FIG. 16A taken along line A-A;

FIGS. 28A and 28B respectively depict front and side views of an exemplary non-limiting embodiment of a shock-sensing device that can be mounted into a hole on a mouth guard according to the subject matter disclosed herein;

FIG. 28C depicts a side view of a non-limiting exemplary embodiment comprising a single post bottom according to the subject matter disclosed herein;

FIG. 28D depicts a side view of a non-limiting exemplary embodiment comprising two post bottoms according to the subject matter disclosed herein;

FIGS. 29A and 29B respectively depict front and side views of another exemplary non-limiting embodiment of a shock-sensing device that can be mounted into a hole on a mouth guard according to the subject matter disclosed herein;

FIG. 29C depicts a side view of a non-limiting exemplary embodiment comprising two post bottoms according to the subject matter disclosed herein;

FIGS. 30A and 30B respectively depict front and side views of yet another exemplary non-limiting embodiment of a shock-sensing device that can be mounted into a hole on a mouth guard according to the subject matter disclosed herein;

FIG. 30C depicts a side view of a non-limiting exemplary embodiment comprising a single post bottom according to the subject matter disclosed herein;

FIG. 30D depicts a side view of a non-limiting exemplary embodiment comprising two post bottoms according to the subject matter disclosed herein;

FIGS. 31A-31C respectively depict front, side and bottom views of an exemplary non-limiting embodiment of a shock-sensing device that can be mounted to the strap of a mouth guard according to the subject matter disclosed herein;

FIG. 31D depicts a side view of a non-limiting exemplary embodiment of a strap that has been modified to receive the exemplary device of FIGS. 31A-31C according to the subject matter disclosed herein; and FIG. 31E depicts a shock-sensing device mounted on the strap of a mouth guard according to the subject matter disclosed herein.

DETAILED DESCRIPTION

Figure 1:
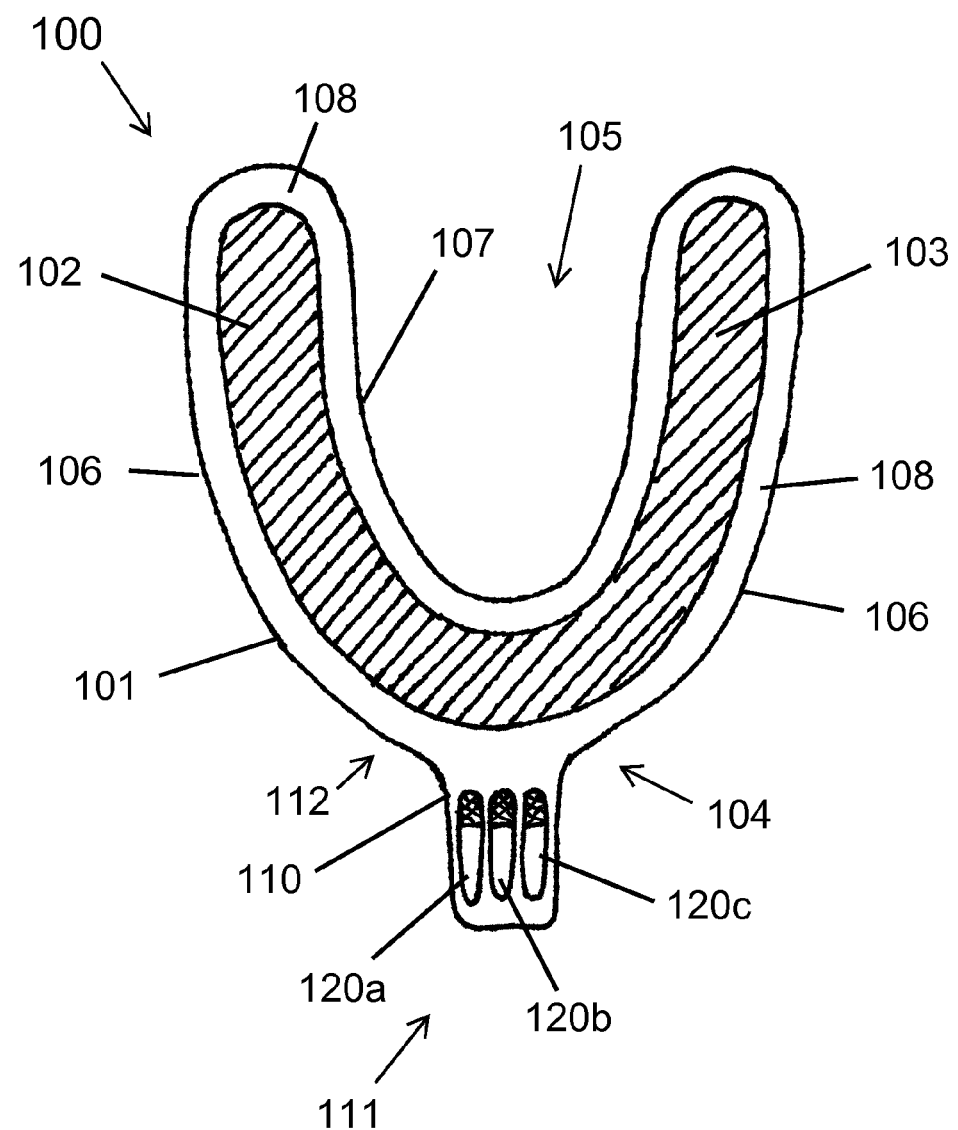
FIG. 1 depicts a top view of one exemplary embodiment of a mouth-guard device according to the subject matter disclosed herein that, in use, is positioned in the mouth of a user for sensing and recording shock experienced by the user.

The word "exemplary" is used herein to mean "serving as an example, instance, or illustration." Any embodiment described herein as "exemplary" is not to be construed as necessarily preferred or advantageous over other embodiments. Additionally, it will be appreciated that for simplicity and/or clarity of illustration, elements illustrated in the figures have not necessarily been drawn to scale. For example, the dimensions of some of the elements may be exaggerated relative to other elements for clarity. Further, in some figures only one or two of a plurality of similar components or items are indicated by reference characters for clarity of the figure. Additionally, as used herein, the term "spill-type-technology" shock-detecting device generally refers to a shock-detecting device in which shock is sensed by a spillage of a component. Similarly, the term "crush-type-technology" shock-detecting device generally refers to a shock-detecting device in which shock is sensed by a component being crushed in some manner.

The subject matter disclosed herein relates to devices that comprise passive (i.e., shock-sensing and indicating) and active (i.e., shock-sensing or detecting and indicating/recording and/or transmitting to separate monitoring devices) shock-sensing and recording or indicating devices. As used herein, the term "shock" means a short-term high-level acceleration and/or deceleration condition. "Intra" or "extra" positioning of active sensing devices provides better correlation to potential injury than conventional techniques or devices. Additionally, as used herein, the terms "shock-sensing device or unit" or "shock-sensing and indicating device or unit" means a passive and/or active shock-sensing and indicating device. Alternatively for convenience, as used herein, the terms "shock-sensing device or unit" or "shock-sensing and indicating device or unit" also means a passive and/or active shock-sensing device with a separate corresponding indicating device.

One exemplary embodiment of a passive shock-sensing and indicating device comprises a passive tube-type sensor/detector/indicator, such as a passive tube-type sensor/detector/indicator commonly known as a ShockWatch® Impact Indicator manufactured by and available from ShockWatch of Dallas, Tex. Further, other passive and/or active shock-sensing and indicating device could comprise non-powered piezoelectric shock-sensing and indicating devices, powered piezoelectric shock-sensing and indicating devices, powered shock-sensing and indicating devices, powered shock-sensing and indicating devices with storage capability and/or RFID-type communication capabilities, and/or powered microaccelerometers. In some exemplary embodiments, both passive and active shock-sensing and indicating devices could be used together. In some exemplary embodiments, one or more shock-sensing and indicating devices could include a close-coupled electromagnetic communications capability. In some exemplary embodiments, the shock-sensing device is separate from a corresponding shock-indicating device.

It should also be understood that the particular exemplary embodiments and configurations of the subject matter disclosed herein, such as particular number, types, orientations of shock-sensing and indicating devices and shock-sensing units, could be combined in ways not specifically disclosed herein. That is, it should also be understood that the particular exemplary embodiments and configurations of the subject matter discloses herein could be combined and/or used together although not specifically disclosed herein as being combined and/or used together. It should be understood that in cases in which components forming the devices and the devices disclosed herein are referred to in the singular, a plurality of such components could also be intended and meant. Similarly, it should be understood that in cases in which components forming the devices and the devices disclosed herein are referred to as a plurality, a singular component could also be intended and meant.

In one exemplary embodiment, a mouth-guard device is configured as a "boil and bite" mouth guard used by, for example, an athlete that participates in contact and/or collision sports, although such exemplary configurations, users and/or uses are not limited by the disclosure herein. In some exemplary embodiments, the shock-sensing and indicating devices, or components, are mounted in conjunction with conventional "tooth guard" devices that provide intimate mechanical connection to the cranial structures. Intimate mechanical connection of a mouth-guard device to the cranial bone mass of a user is achieved by intra-oral positioning and by dental and mandibular contact, thereby allowing the shock-sensing and indicating components of the subject matter disclosed herein to more accurately reflect potential shock-associated injuries (concussive brain injury and other) that could be caused by shocks experienced by the user. In one exemplary embodiment, extra-oral positioning of visually indicating passive and/or active shock-sensing and indicating components provides others, such as other players, referees, coaches, on-site medical personnel and/or parents, "real-time evidence" that the user has experienced a potential injury-level shock without the mouth-guard device being removed from the user's mouth. In another exemplary embodiment, the mouth-guard device is removed from the mouth of a user to view the shock-sensing and indicating components. In yet another exemplary embodiment, the extra-oral positioning of visually indicating passive and/or active shock-sensing and indicating components provide an indication of progressive levels of shock exposure and a corresponding probability of potential injury.

In one exemplary embodiment of the subject matter disclosed herein, the passive mechanical shock-sensing and indicating devices could be "replace-after-tripped" devices. In another exemplary embodiment, the passive mechanical shock-sensing and indicating devices are re-settable. In still another exemplary embodiment, the passive shock-sensing and indicating devices are not re-settable or replaceable. In one exemplary embodiment, the shock-sensing and indicating devices are oriented along substantially orthogonal axes. In another exemplary embodiment, each shock-sensing and indicating device of a pair of shock-sensing devices is oriented in substantially opposite directions along a given axis. In still another exemplary embodiment, one or more shock-sensing and indicating devices could be positioned at selected locations on and/or in a mouth guard with a selected location being dependent upon the particular application for which the mouth guard is intended.

FIG. 1 depicts a top view of one exemplary embodiment of a mouth-guard device 100 that, in use, is positioned in the mouth of a user, or wearer, for sensing and recording shock experienced by the user. Mouth-guard device 100 comprises a base member 101 comprising a generally arcuate shape or U-shape. Base member 101 comprises a first biting surface 102 and a second biting surface 103 that, in use, are positioned between occlusal tooth surfaces (not shown) of a user's upper and lower teeth (not shown). Base member 101 also comprises an anterior portion 104, a posterior portion 105, a labial-buccal side 106, and a lingual side 107, and at least one flange 108 extending from either the labial-buccal side 106 or the lingual side 108 of base member 101. When mouth-guard device 100 is inserted into the user's mouth, anterior portion 104 is proximate to the opening of the user's mouth and posterior portion is proximate to the user's molars. The labial-buccal side 106 is proximate to a user's inner cheeks, while the lingual side 107 is proximate to the user's tongue when mouth-guard device 100 is inserted into the user's mouth. Flanges 108 can extend in a superior (upper) and/or inferior (lower) direction and are respectively shaped to form a barrier between a user's upper and lower teeth (not shown) and a user's soft oral tissue (not shown).

A handle (or tongue) 110 is affixed to anterior portion 104 of mouth-guard device 100. Handle 100 has a distal end 111 and a proximate end 112. In one exemplary embodiment, proximate end 112 of handle 110 is affixed to the anterior portion 104 of mouth-guard device 100. Handle 100 can be shaped and sized so that the distal end 111 extends out of the user's mouth. In one exemplary embodiment, a central planar axis (not shown) with which the handle 110 is aligned is substantially co-planar with a central planar axis (not shown) upon which base member 101 is substantially aligned. In another exemplary embodiment, the central planar axis (not shown) of handle 110 is substantially not co-planar with respect to the central planar axis (not shown) of the base member 101.

In one exemplary embodiment, at least one shock-sensing and indicating device 120 is affixed to handle 110 in a well-known manner. The specific exemplary embodiment depicted in FIG. 1 comprises three shock-sensing and indicating devices 120a-120c that are affixed to handle 110 in a well-known manner. In one exemplary embodiment, the shock-sensing and indicating devices of the mechanical system shown in FIG. 1 (and for other shock-sensing devices and/or shock-sensing and indicating devices disclosed herein) could be selected to indicate whether one or more specific levels of shock have been experienced by the shock-sensing and indicating device. In another exemplary embodiment, the one or more specific levels of shock detected by the shock-sensing and indicating devices is selected from a range of about 50 g of shock to about 100 g of shock. In still another exemplary embodiment, the one or more specific levels of shock detected by the shock-sensing and indicating devices is/are selected from the range of about 50 g of shock to about 250 g of shock. In still other exemplary embodiments, the shock level detected by a shock-sensing and indicating device could be greater than about 250 gs of shock. In yet another exemplary embodiment, the specific levels of shock indication could be selected to be standard graduated levels, such as, about 50 g, about 75 g, and about 100 g. It should be understood that the shock-sensing and indicating devices of the subject matter disclosed herein could sense and indicate shock levels outside the range of about 50 g of shock to about 100 g of shock. In another exemplary embodiment, one or more selected levels of shock indication could be custom selected for a particular application. Additionally, it should be understood that particular exemplary embodiments of the mechanical system depicted in FIG. 1 and elsewhere herein could comprise more or fewer shock-sensing and indicating devices than what is depicted in a given figure.

In one exemplary embodiment, mouth-guard device 100, as well as other exemplary embodiments of mouth-guard devices disclosed herein, is made of a thermoplastic that becomes moldable at a glass transition temperature that is greater than the temperature in the user's mouth. In one exemplary embodiment, mouth-guard device 100 is made from a thermoplastic having a glass transition temperature greater than about 95 degrees Fahrenheit. In another exemplary embodiment, the thermoplastic becomes suitable for molding mouth-guard device 100 to a user's upper and lower teeth at a temperature less than about 180 degrees Fahrenheit. A thermoplastic with a glass transition temperature greater than about 180 degrees Fahrenheit could be used to form the mouth-guard device of the subject matter disclosed herein, provided that the mouth-guard device is fitted to dental models of a person's teeth while the thermoplastic is in the moldable state and allowed to cool prior to use as a protective device. Exemplary thermoplastics suitable for a mouth-guard device include, but are not limited to, ethylene vinyl alcohol, ethylene vinyl acetate, urethane, styrene block copolymer, rubber, polystyrene, polybutadiene, polyisoprene, polyolefin, organopolysiloxane, alicyclic saturated hydrocarbon resin, polycaprolactone, polyethylene, unfilled polycarbonate, ester gum, polyethylenetetraphthalate, terpolymer, nylon, nylon copolymer, polyester, copolyester, or any combination of one or more thereof.

FIGS. 2A-2C depict an exemplary embodiment of a mouth-guard device 200 that comprises three shock-sensing and indicating devices (or shock-detecting devices) 201a-201c that, in use, is positioned in the mouth of a user for sensing and recording shock experienced by the user. In particular, FIG. 2A depicts a top view of the exemplary embodiment of mouth-guard device 200. FIG. 2B depicts a front view of the exemplary embodiment of mouth-guard device 200, and FIG. 2C depicts a side view of the exemplary embodiment of mouth-guard device 200. For the exemplary embodiment depicted in FIGS. 2A-2C, mouth-guard device 200 comprises three (3) shock-sensing and indicating devices 201a-201c that are attached to mouth-guard device 200, and respectively positioned and oriented along substantially orthogonal axes. It should be understood that mouth-guard device 200 is depicted using dashed lines because the exact configuration of mouth-guard device 200 could vary for the particular application for mouth-guard device 200 is intended. It should also be understood that shock-sensing and indicating devices 201a-201c could be positioned internally to mouth-guard device 200, in which case, the material forming mouth-guard device 200 would be permit viewing of shock-sensing and indicating devices 201a-201c, and/or could be attached to a surface of device 200 in a well-known manner. Further still, it should be understood that the particular orientation of a shock-sensing and indicating device 201 along an axis could be in either direction along the axis, and that each shock-sensing device 201 could have the same or substantially the same shock-level sensing capability, or could have a different selected shock-level sensing capability than another shock-sensing and indicating device 201.

Figure 3A:
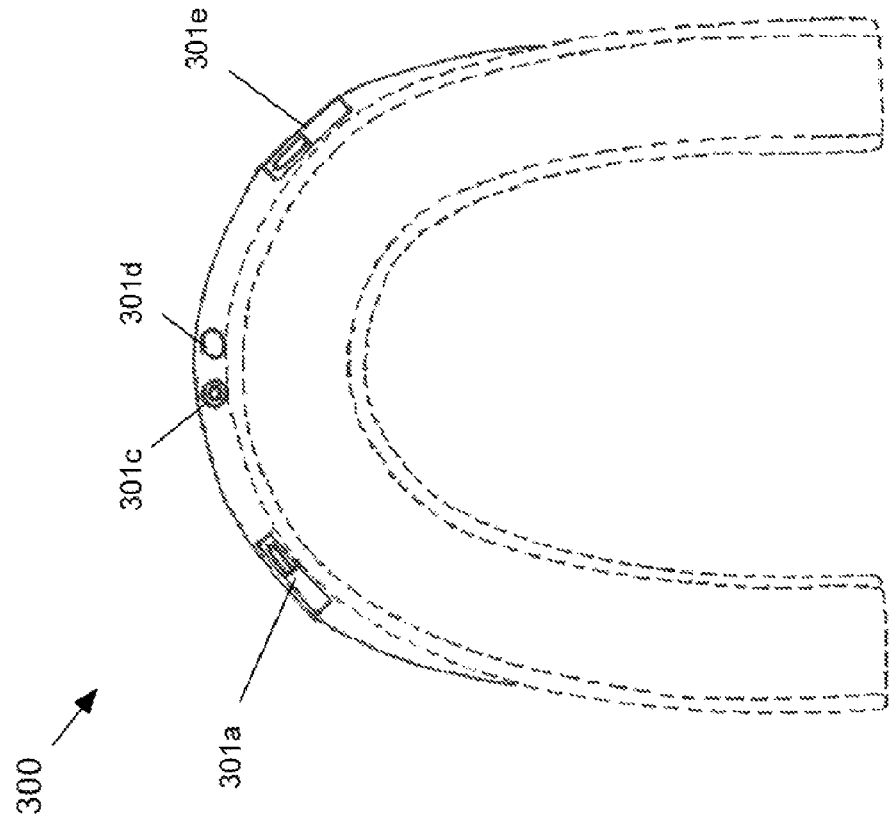
FIGS. 3A-3C respectively depict top, front and side view of an exemplary embodiment of a mouth-guard device that comprises six shock-sensing and indicating devices that, in use, is positioned in the mouth of a user for sensing and recording shock experienced by the user.
Figure 3B:
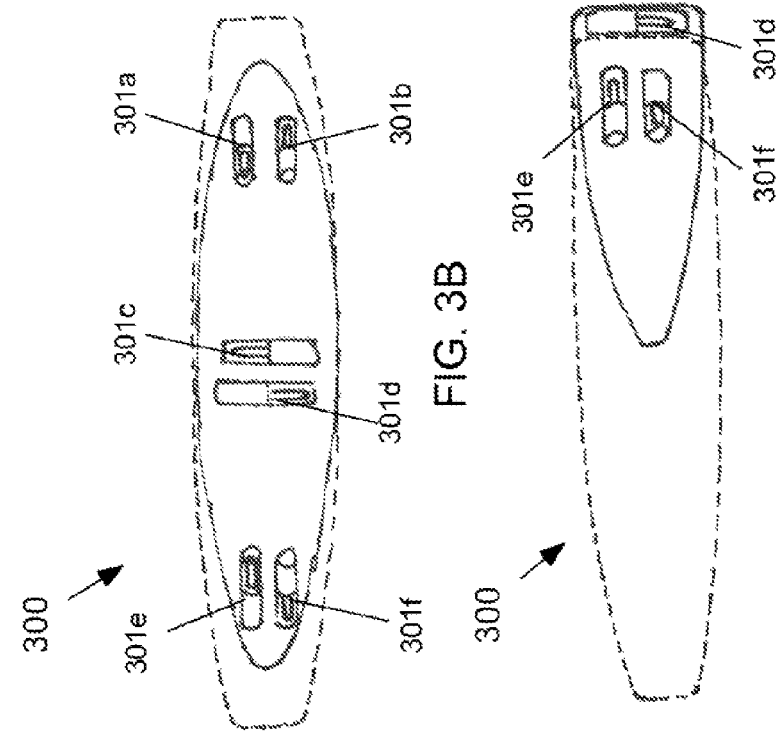
Figure 3C:
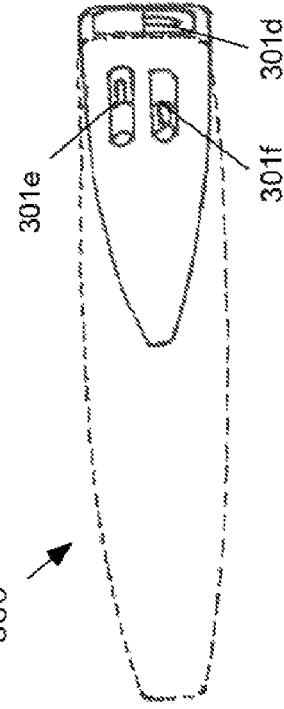

FIGS. 3A-3C depict an exemplary embodiment of a mouth-guard device 300 that comprises six shock-sensing and indicating devices (or shock-detecting devices) 301a-301f that, in use, is positioned in the mouth of a user for sensing and recording shock experienced by the user. In particular, FIG. 3A depicts a top view of the exemplary embodiment of mouth-guard device 300. FIG. 3B depicts a front view of the exemplary embodiment of mouth-guard device 300, and FIG. 3C depicts a side view of the exemplary embodiment of mouth-guard device 300. For the exemplary embodiment depicted in FIGS. 3A-3C, mouth-guard device 300 comprises six (6) shock-sensing devices 301a-301f that are attached to mouth-guard device 300, and respectively positioned and oriented along substantially orthogonal axes. More specifically, a pair of shock-sensing and indicating devices 301 is bi-directionally oriented along each respective substantially orthogonal axis. It should be understood that mouth-guard device 300 is depicted using dashed lines because the particular configuration of mouth-guard device 300 could vary for the particular application for mouth-guard device 300 is intended. It should also be understood that shock-sensing and indicating devices 301a-301f could be positioned internally to mouth-guard device 300, in which case, the material forming device mouth-guard 300 would be permit viewing of shock-sensing and indicating devices 301a-301c, and/or could be attached to a surface of mouth-guard device 300 in a well-known manner. Further still, it should be understood that the particular orientation of a shock-sensing device 301 along an axis could be in either direction along the axis, and that each shock-sensing and indicating device 301 could have the same or substantially the same shock-level sensing capability, or could have a different selected shock-level sensing capability than another shock-sensing and indicating device 301.

FIGS. 4A-4C depict an exemplary embodiment of a mouth-guard device 400 that comprises one shock-sensing and indicating device (or shock-detecting device) 401 that, in use, is positioned in the mouth of a user for sensing and recording shock experienced by the user. In particular, FIG. 4A depicts a top view of the exemplary embodiment of mouth-guard device 400. FIG. 4B depicts a front view of the exemplary embodiment of mouth-guard device 400, and FIG. 4C depicts a side view of the exemplary embodiment of mouth-guard device 400. For the exemplary embodiment depicted in FIGS. 4A-4C, mouth-guard device 400 comprises one shock-sensing device 401 that is attached to the mouth-guard device and positioned and oriented along a selected axis. It should be understood that mouth-guard device 400 is depicted using dashed lines because the particular configuration of mouth-guard device 400 could vary for the particular application for mouth-guard device 400 is intended. It should also be understood that shock-sensing device and indicating 401 could be positioned internally to mouth-guard device 400, in which case, the material forming mouth-guard device 400 would be permit viewing of shock-sensing and indicating device 401, or could be attached to a surface of mouth-guard device 400 in a well-known manner. Further still, it should be understood that the particular orientation of a shock-sensing and indicating device 401 along an axis could be in either direction along the axis. Moreover, it should be understood that the particular axis and orientation of shock-sensing device and indicating 401 depicted in FIGS. 4A-4C is only exemplary and is not limiting.

FIGS. 5A-5C respective depict front, right-side and bottom views of an exemplary embodiment of a shock-sensing unit 500 comprising four passive-shock-sensing devices 501, such as passive-tube-type sensor/detector/indicators, that are suitable for use with the subject matter disclosed herein. For the shock-sensing unit 500 depicted in FIGS. 5A-5C, shock-sensing devices 501 are encapsulated, such as by clear molded or a translucent plastic 502, such as polycarbonate or copolyester, on a suitable substrate 503, such as a silicone, a potting compound or an epoxy. It should be understood that other suitable materials could be used to for molded plastic 502 and for substrate 503. While shock-sensing unit 500 is depicted as comprising a disk shape, it should be understood that other suitable shapes could be used.

Figure 6C:
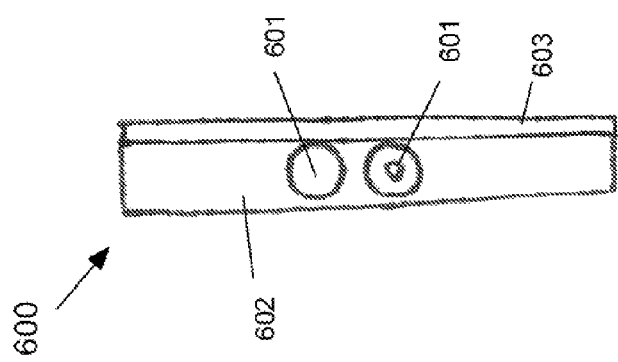
FIGS. 6A-6C respectively depict front, right-side and bottom views of an exemplary embodiment of a shock-sensing unit comprising two passive-shock-sensing devices, such as passive-tube-type sensor/detector/indicators, that are suitable for use with the subject matter disclosed herein.
Figure 6A:
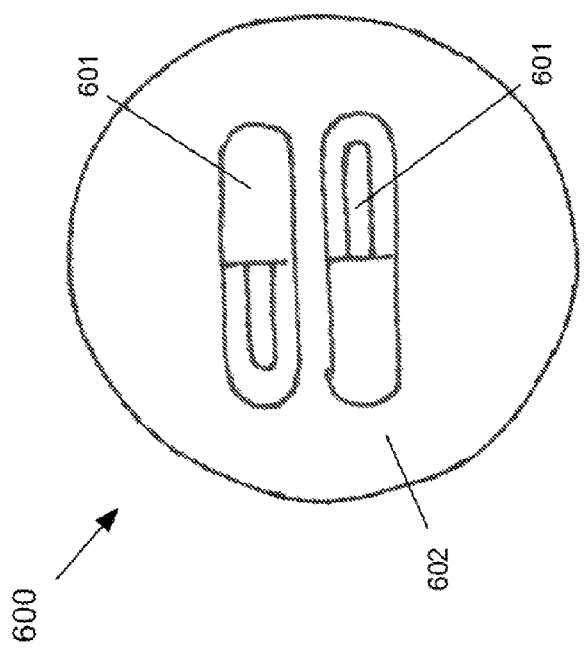
Figure 6B:
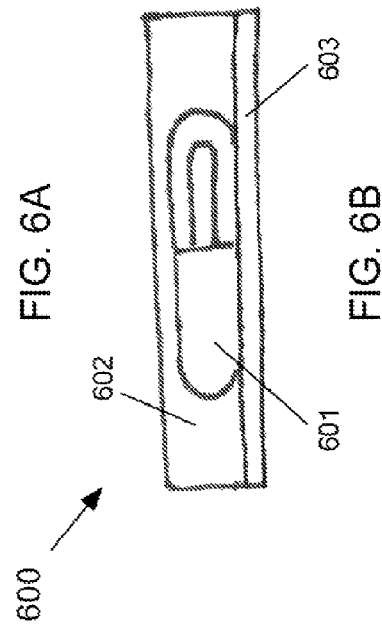

FIGS. 6A-6C respectively depict front, right-side and bottom views of an exemplary embodiment of a shock-sensing unit 600 comprising two passive-shock-sensing devices 601, such as passive-tube-type sensor/detector/indicators, that are suitable for use with the subject matter disclosed herein. For the shock-sensing unit 600 depicted in FIGS. 6A-6C, shock-sensing devices 601 are encapsulated, such as by clear or a translucent molded plastic 602, such as polycarbonate or copolyester, on a suitable substrate 603, such as a silicone, a potting compound or an epoxy. It should be understood that other suitable materials could be used for molded plastic 602 and for substrate 603. While shock-sensing unit 600 is depicted as comprising a disk shape, it should be understood that other suitable shapes could be used.

FIGS. 7A-7C respectively depict front, right-side and bottom views of an exemplary embodiment of a shock-sensing unit 700 comprising one passive-shock-sensing device 701, such as a passive-tube-type sensor/detector/indicator, that are suitable for use with the subject matter disclosed herein. For the shock-sensing unit 700 depicted in FIGS. 7A-7C, shock-sensing device 701 is encapsulated, such as by a bubble of clear or a translucent plastic 702, such as polycarbonate or copolyester, on a suitable substrate 703, such as a silicone, a potting compound or an epoxy. It should be understood that other suitable materials could be used for molded plastic 702 and for substrate 703. While shock-sensing unit 700 is depicted as comprising a disk shape, it should be understood that other suitable shapes could be used.

Figure 8C:
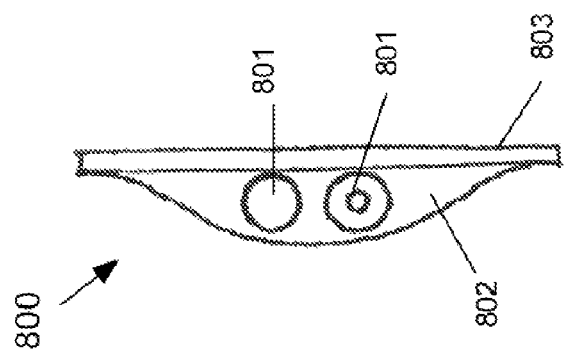
FIGS. 8A-8C respectively depict front, right-side and bottom views of an exemplary embodiment of a shock-sensing unit comprising two passive-shock-sensing devices, such as passive-tube-type sensor/detector/indicators, that are suitable for use with the subject matter disclosed herein.
Figure 8A:
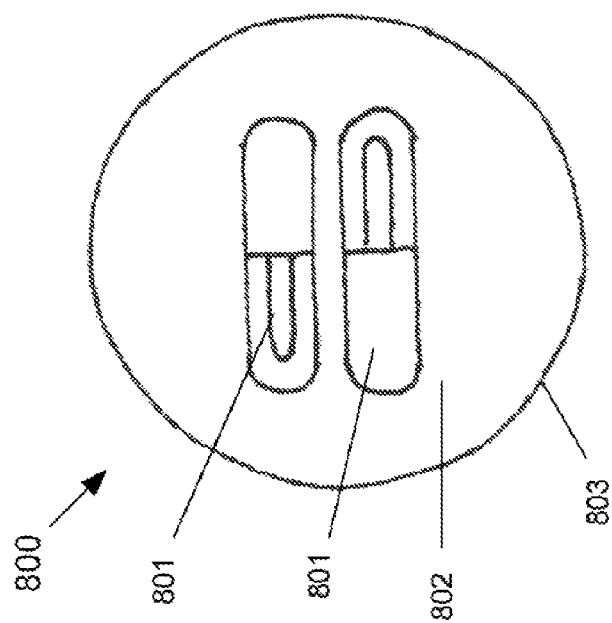
Figure 8B:
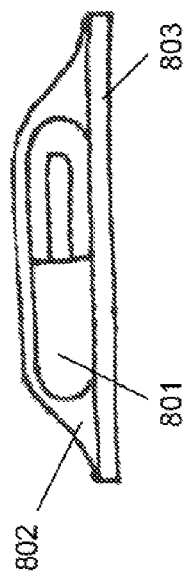

FIGS. 8A-8C respectively depict front, right-side and bottom views of an exemplary embodiment of a shock-sensing unit 800 comprising two passive-shock-sensing devices 801, such as passive-tube-type sensor/detector/indicators, that are suitable for use with the subject matter disclosed herein. For the shock-sensing unit 800 depicted in FIGS. 8A-8C, shock-sensing device 801 is encapsulated, such as by a bubble of clear or a translucent plastic 802, such as polycarbonate or copolyester, on a suitable substrate 803, such as a silicone, a potting compound or an epoxy. It should be understood that other suitable materials could be used for molded plastic 802 and for substrate 803. While shock-sensing unit 800 is depicted as comprising a disk shape, it should be understood that other suitable shapes could be used.

One exemplary embodiment of the subject matter disclosed herein comprises one or more passive and/or active shock-sensing devices that are integrally formed into a shock-sensing unit that could be attached to the body of a user using, for example, an adhesive coating on a surface of the shock-sensing unit. In another exemplary embodiment, the shock-sensing unit could be attached to a piece of equipment, such as a helmet, an eye-protection device, or clothing worn by a user.

Figure 9A:
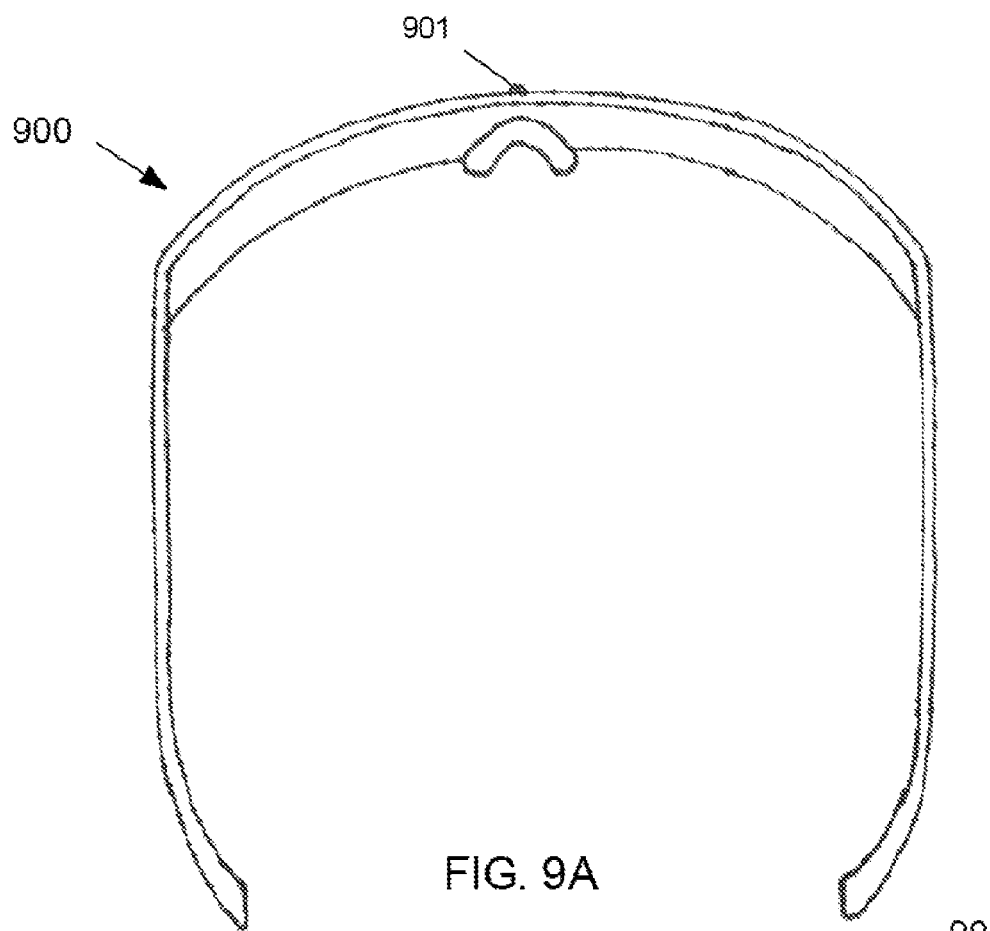
FIGS. 9A-9C respectively depict top, front and left-side views of an exemplary embodiment of an eye-protection device comprising one passive-shock-sensing device, such as a passive-tube-type sensor/detector/indicator.
Figure 9B:
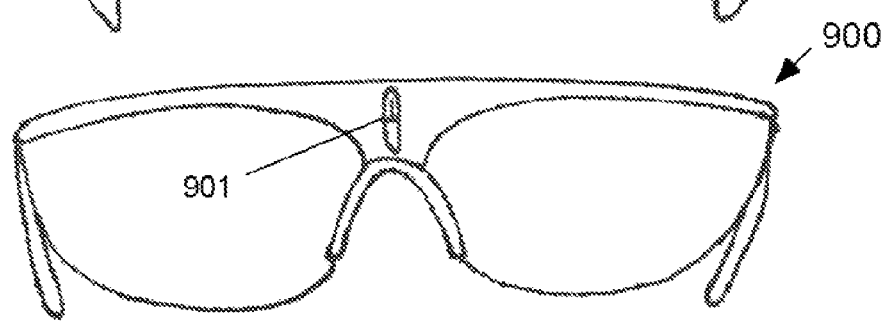
Figure 9C:
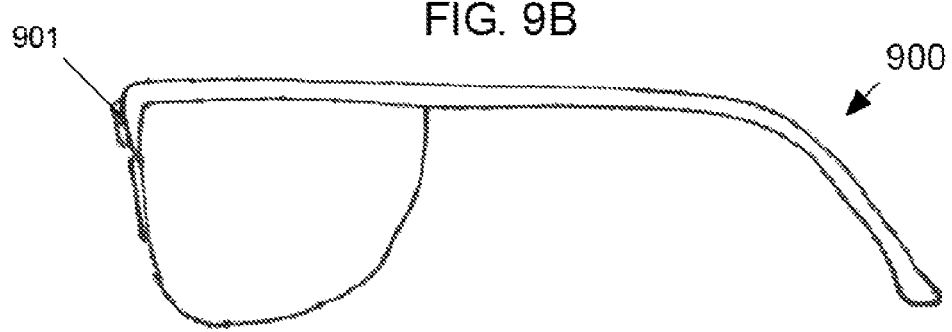

FIGS. 9A-9C respectively depict top, front and left-side views of an exemplary embodiment of an eye-protection device 900 comprising one passive-shock-sensing device 901, such as a passive-tube-type sensor/detector/indicator. As depicted, shock-sensing device 901 is attached to eye-protection device 900 at the bridge of eye-protection device 900. While device 900 is referred to as an eye-protection device, it should be understood that device 900 is not so limited and could, in one exemplary embodiment, be a pair of corrective-lens glasses and in another exemplary embodiment be a pair of sunglasses. It should also be understood that the orientation and/or position of shock-sensing device 901 is only exemplary and could be different than that depicted in FIGS. 9A-9C. Moreover, it should be understood that device 900 could be configured in one exemplary embodiment as a pair of goggles.

Figure 10A:
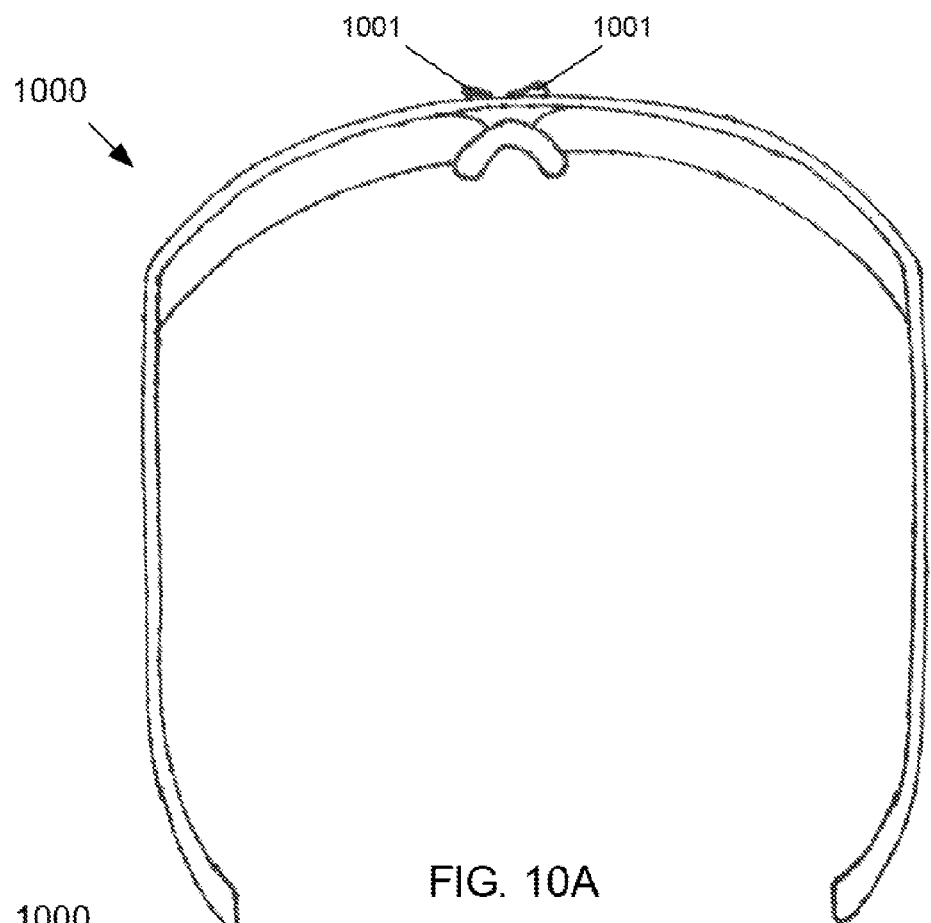
FIGS. 10A-10C respectively depict top, front and left-side views of an exemplary embodiment of an eye-protection device comprising two passive-shock-sensing devices, such as passive-tube-type sensor/detector/indicators.
Figure 10B:
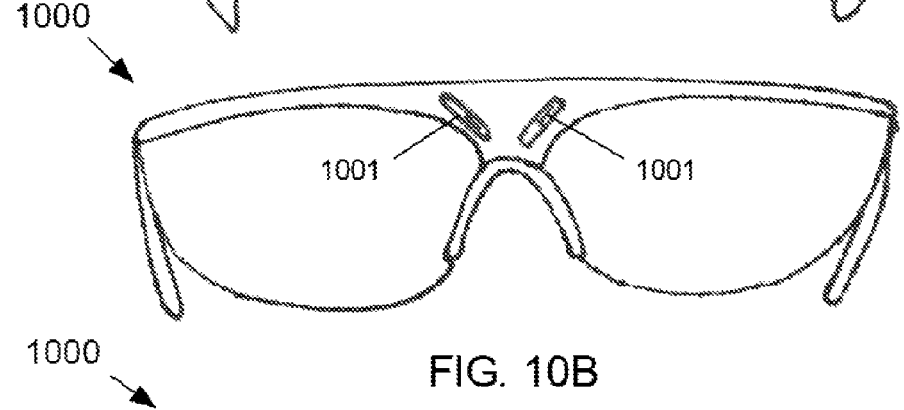
Figure 10C:
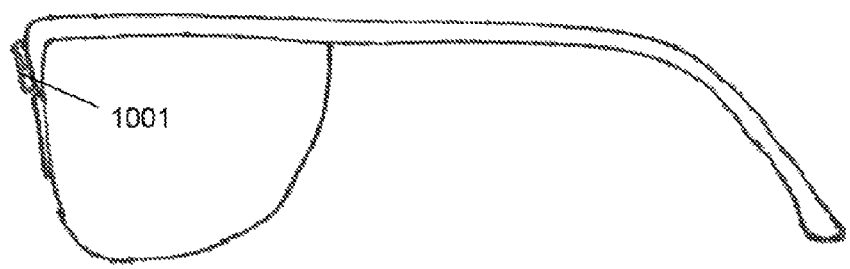

FIGS. 10A-10C respectively depict top, front and left-side views of an exemplary embodiment of an eye-protection device 1000 comprising two passive-shock-sensing devices 1001, such as passive-tube-type sensor/detector/indicators. As depicted, shock-sensing device 1001 is attached to eye-protection device 1000 at the bridge of eye-protection device 1000. While device 1000 is referred to as an eye-protection device, it should be understood that device 1000 is not so limited and could, in one exemplary embodiment, be a pair of corrective-lens glasses and in another exemplary embodiment be a pair of sunglasses. It should also be understood that the orientation and/or position of shock-sensing devices 1001 is only exemplary and could be different than that depicted in FIGS. 10A-10C. Moreover, it should be understood that device 1000 could be configured in one exemplary embodiment as a pair of goggles.

Figure 11A:
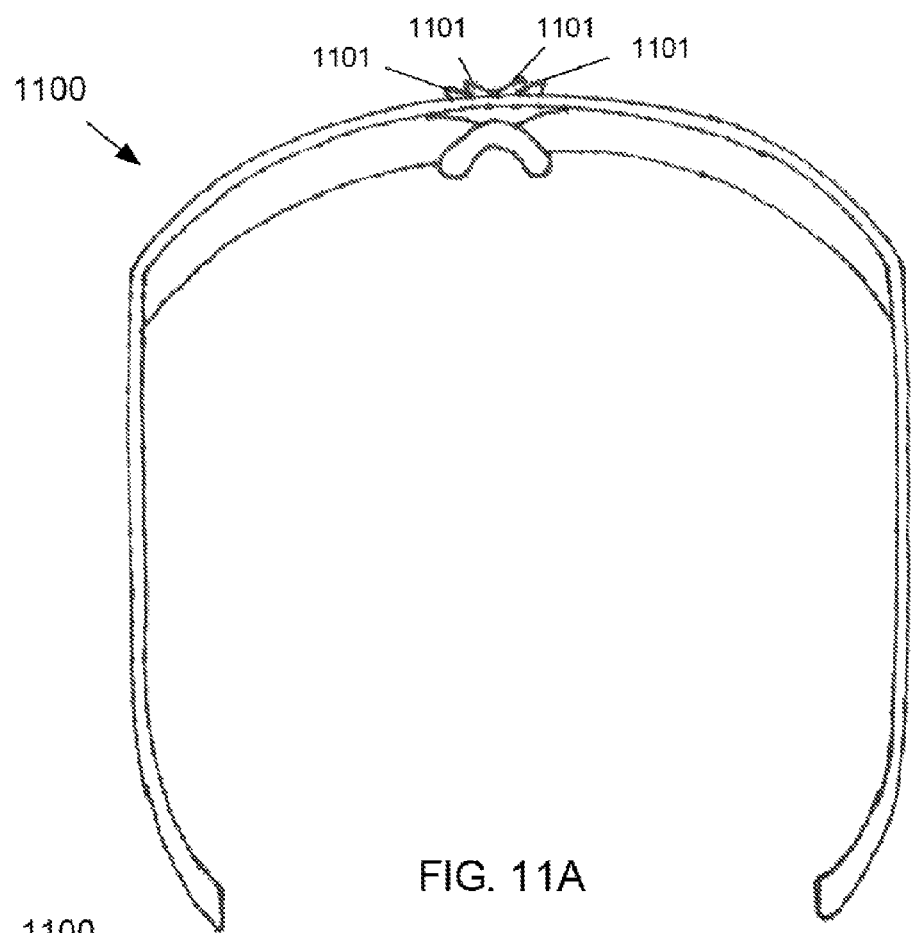
FIGS. 11A-11C respectively depict top, front and left-side views of an exemplary embodiment of an eye-protection device comprising four passive-shock-sensing devices, such as passive-tube-type sensor/detector/indicators.
Figure 11B:
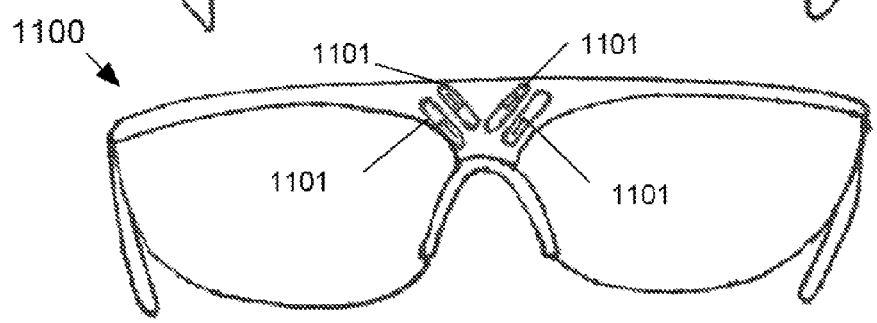
Figure 11C:
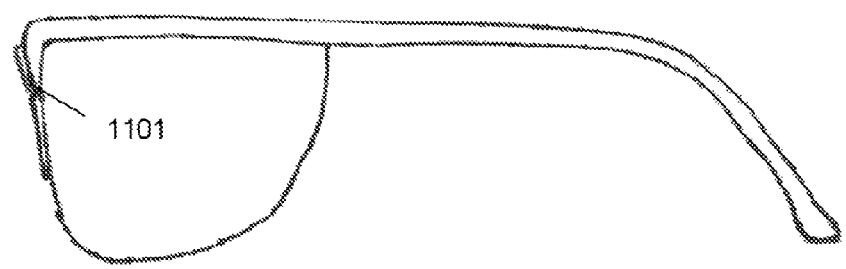

FIGS. 11A-11C respectively depict top, front and left-side views of an exemplary embodiment of an eye-protection device 1100 comprising four passive-shock-sensing devices 1101, such as passive-tube-type sensor/detector/indicators. As depicted, shock-sensing devices 1101 are attached to eye-protection device 1100 at the bridge of eye-protection device 1100 so that each shock-sensing device 1101 of a pair of shock-sensing devices is oriented in different directions along a selected axis. While device 1100 is referred to as an eye-protection device, it should be understood that device 1100 is not so limited and could, in one exemplary embodiment, be a pair of corrective-lens glasses and in another exemplary embodiment be a pair of sunglasses. It should also be understood that the orientation and/or position of pairs of shock-sensing devices 1101 is only exemplary and could be different than that depicted in FIGS. 11A-11C.

Moreover, it should be understood that device 1100 could be configured in one exemplary embodiment as a pair of goggles.

Figure 12A:
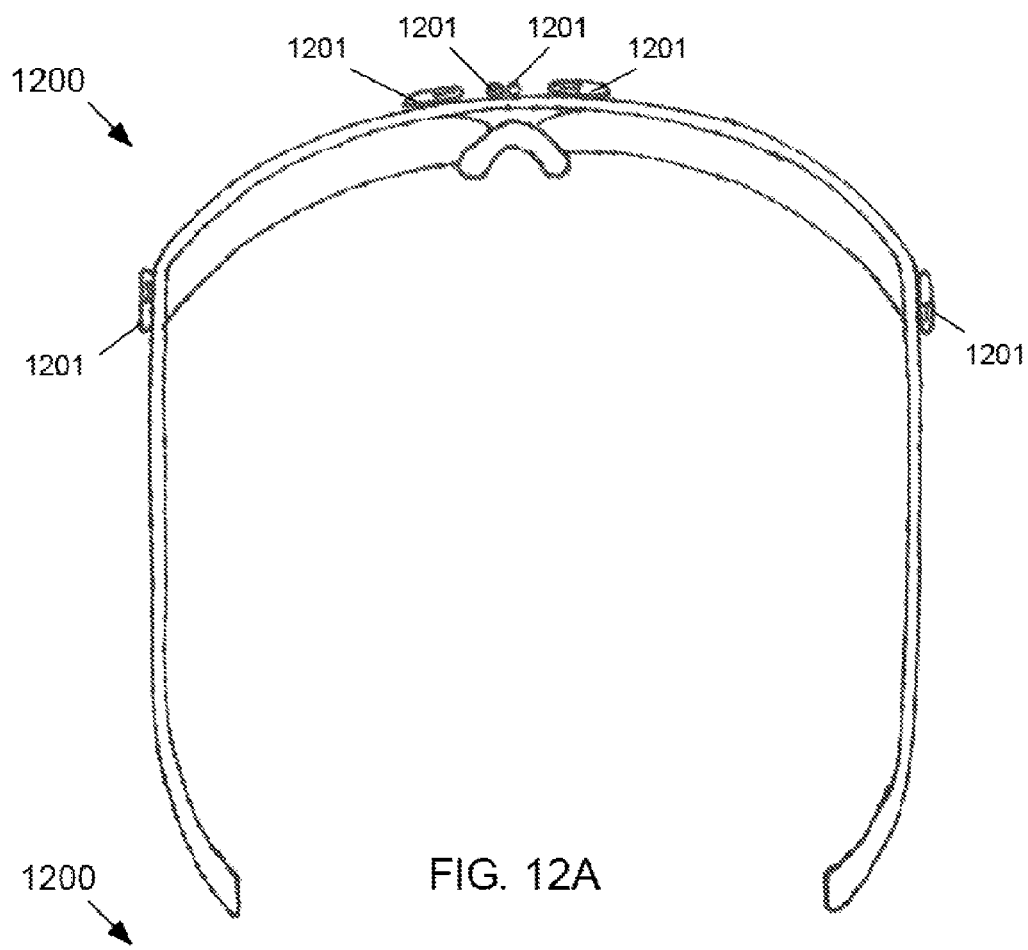
FIGS. 12A-12C respectively depict top, front and left-side views of an exemplary embodiment of an eye-protection device comprising six passive-shock-sensing devices, such as passive-tube-type sensor/detector/indicators.
Figure 12B:
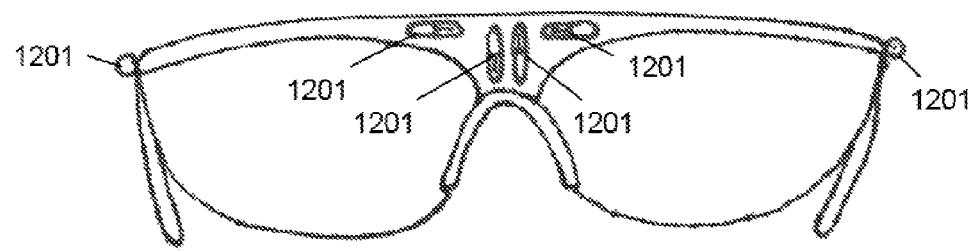
Figure 12C:
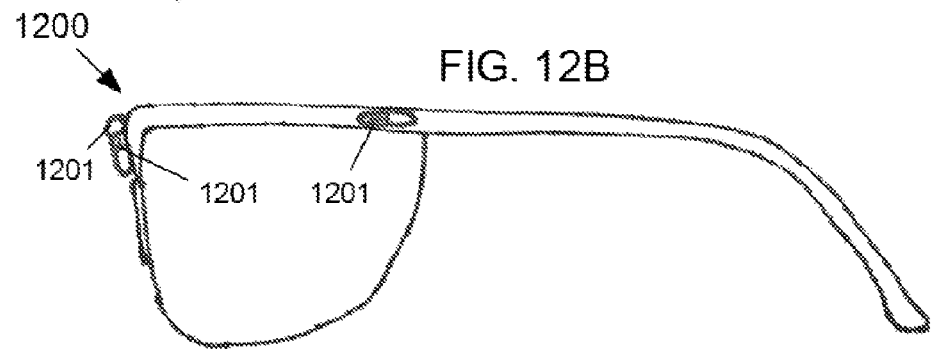

FIGS. 12A-12C respectively depict top, front and left-side views of an exemplary embodiment of an eye-protection device 1200 comprising six passive-shock-sensing devices 1201, such as passive-tube-type sensor/detector/indicators. As depicted, four shock-sensing devices 1201 are attached to eye-protection device 1200 at the bridge of eye-protection device 1200 and one on each ear piece of device 1200. The particular orientation of each shock-sensing device 1201 is selected so that there is another shock-sensing device 1201 oriented in a direction that opposite to shock-sensing device. While device 1200 is referred to as an eye-protection device, it should be understood that device 1200 is not so limited and could, in one exemplary embodiment, be a pair of corrective-lens glasses and in another exemplary embodiment be a pair of sunglasses. It should also be understood that the orientation and/or position of pairs of shock-sensing devices 1201 is only exemplary and could be different than that depicted in FIGS. 12A-12C. Moreover, it should be understood that device 1200 could be configured in one exemplary embodiment as a pair of goggles.

FIGS. 13A-13C respectively depict front, right-side and bottom views of an exemplary embodiment of a shock-sensing unit 1300 comprising three passive-shock-sensing devices 1301, such as passive-tube-type sensor/detector/indicators. For the shock-sensing unit 1300 depicted in FIGS. 13A-13C, shock-sensing devices 1301 are encapsulated, such as by clear or a translucent molded plastic 1302, such as polycarbonate or copolyester, on a suitable substrate 1303, such as a silicone, a potting compound or an epoxy. It should be understood that other suitable materials could be used for molded plastic 1302 and for substrate 1303. In one exemplary embodiment, shock-sensing devices 1301 could be selected to indicate whether one or more specific levels of shock, selected from a range of about 50 g of shock to about 100 g of shock, have been experienced by the shock-sensing device. In another exemplary embodiment, the specific levels of shock indication could be selected to be standard graduated levels, such as, about 50 g, about 75 g, and about 100 g. In another exemplary embodiment, one or more selected levels of shock indication could be custom selected for a particular application. It should be understood that shock-sensing devices 1301 could sense/detect/indicate shock levels outside the range of about 50 g of shock to about 100 g of shock. Additionally, it should be understood that another exemplary embodiment could comprise more or fewer shock-sensing devices than what is depicted in FIGS. 13A-13C. While shock-sensing unit 1300 is depicted as comprising a disk shape, it should be understood that other suitable shapes could be used.

One exemplary embodiment of the subject matter disclosed herein comprises one or more passive and/or active shock-sensing devices that are attached to and/or integrally formed with an adhesive strip, similar to a nasal strip or an adhesive bandage, that could be worn by a user by affixing the adhesive surface of the adhesive strip to the skin of the user, such as, but not limited to, across the bridge of a nose, a forehead or a side of a face.

FIGS. 14A-14C respectively depict front, side and end views of an exemplary embodiment of a shock-sensing unit 1400 comprising two shock-sensing devices 1401 attached in a well-known manner to a substrate 1402 having an adhesive coating that is used for attaching shocking-sensing unit 1400 to the body of a user, or to a piece of equipment or clothing worn by the user. The particular exemplary embodiment of shock-sensing device 1400 depicted in FIGS. 14A-14C comprises an adhesive nasal strip 1402. FIG. 14D depicts shock-sensing device 1400 being worn as an adhesive nasal strip by a user. It should also be understood that the particular orientation of shock-sensing devices 1401 is only exemplary and could be different than that depicted in FIGS. 14A-14C. Additionally, it should be understood that another exemplary embodiment could comprise more or fewer shock-sensing devices than what is depicted in FIGS. 14A-14C. While shock-sensing unit 1400 is depicted as comprising an adhesive strip, it should be understood that other suitable shapes could be used.

FIGS. 15A-15C respectively depict front, side and bottom views of an exemplary embodiment of a shock-sensing unit 1500 comprising six shock-sensing devices 1501 attached in a well-known manner to a substrate 1502 having an adhesive coating that is used for attaching shocking-sensing unit 1500 to the body of a user, or to a piece of equipment or clothing worn by the user. The particular exemplary embodiment of shock-sensing device 1500 depicted in FIGS. 15A-15C comprises an adhesive nasal strip 1502 so that, in use, the orientation of the pairs of shock-sensing devices 1501 provide bi-directional shock-detecting capability along substantially orthogonal axis. FIG. 15D depicts shock-sensing device 1500 being worn as an adhesive nasal strip by a user. It should also be understood that the particular orientation of shock-sensing devices 1501 is only exemplary and could be different than that depicted in FIGS. 15A-15C. Additionally, it should be understood that another exemplary embodiment could comprise more or fewer shock-sensing devices than what is depicted in FIGS. 15A-15C. While shock-sensing unit 1500 is depicted as comprising a generally triangularly shaped adhesive strip, it should be understood that other suitable shapes could be used.

One exemplary embodiment of the subject matter disclosed herein comprises one or more passive and/or active shock-sensing devices that are attached to and/or integrally formed with an ear-plug device could be worn by a user by placing the ear-plug device in the ear of the user. Still another exemplary embodiment of the subject matter discloses herein comprises one or more passive and/or active shock-sensing devices that are configured in an ear-mounted device that does not occlude the ear canal of the ear.

FIGS. 16A and 16B respectively depict front and side views of an exemplary embodiment of a shock-sensing unit configured to fit into the ear of a user and comprising one shock-sensing device. FIG. 16C is a cross-sectional view of the exemplary embodiment of the shock-sensing unit depicted in FIG. 16A taken along line A-A. The particular exemplary embodiment of shock-sensing unit 1600 depicted in FIGS. 16A-16C can be worn in the ear canal of a user and can be formed from silicone. It should be understood that other suitable materials could be used to form shock-sensing unit. In another exemplary embodiment, two or more shock-sensing devices could be used for shock-sensing unit 1600.

One exemplary embodiment of a passive shock-sensing and indicating device according to the subject matter disclosed herein comprises a two-component chemical reaction that results in a simple color change, chemi-luminescent output, or electro-chemical output when a shock of a certain level is sensed by the shock-sensing and indicating device. For this approach, one component (or compound) is held a reservoir-type tube through capillary, vacuum, and/or thixotropic properties. A first component (or compound) is released into an enclosure containing a second component (or compound) that could be solid or liquid, and unrestrained, or a substrate or carrier that is impregnated, surface coated or bonded with the second component (or compound) that is inserted into the enclosure, or impregnated into a carrier capable of being inserted into the enclosure. It should be understood that, although a two-component chemical reaction system is described, more than two components, i.e., multiple components, could actually comprise the chemical reaction system.

Two-component chemi-luminescent reactions that are suitable for use with the subject matter disclosed herein include a luminol reaction and an oxalate reactions, which are also commonly used for light sticks and glow sticks. In one exemplary embodiment, a two-component chemi-luminescent reaction is based on bis(2,4,5-trichlorophenyl-6-carbopentoxyphenyl)oxalate (CPPO) reacting with hydrogen peroxide include fluorophors (FLR) that are the chemicals that provide the color for the chemi-luminescent reaction. In another exemplary embodiment, a two-component chemi-luminescent reaction is based on bis(2,4,6-trichlorophenyl)oxlate (TCPO) reacting with hydrogen peroxide: Exemplary fluorescent dyes that may be added to a chemi-luminescent chemical reaction to release different colors of light include, but are not limited to, Blue 9,10-diphenylanthracene; Green 9,10-bis(phenylethynyl)anthracene, Yellow 1-chloro-9,10-bis(phenylethynyl)anthracene, and Orange 5,12-bis(phenylethynyl)-naphthacene. Red fluorophors, such as Rhodamine B could also be used as a fluorescent dye, however, such red-emitting dyes are not typically used in an oxalate reaction because the red fluorophors are not stable when stored with the other chemicals that are part of the chemi-luminescent reaction. Instead, in one exemplary embodiment, a fluorescent red pigment could be molded into the plastic tube that encases the chemi-luminescent components. The red-emitting pigment absorbs the light from, for example, a high-yield (bright) yellow reaction and re-emits the light as red, thereby resulting in an apparent red chemi-luminescent reaction that is approximately twice as bright as it would have been had the chemi-luminescent used a red fluorophor in the two-compound solution. It should be understood that the subject matter disclosed herein is not limited to a two-component chemical reaction system, but could be a multi-component chemical reaction system comprising, but not limited to, components disclosed herein as bring suitable.

Figure 17A:
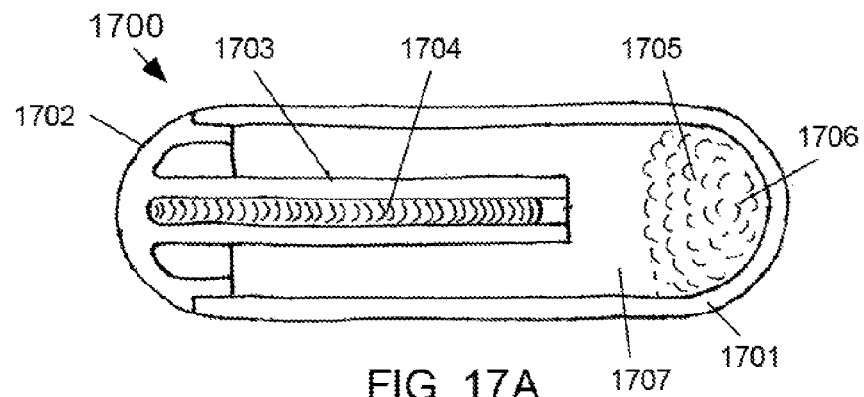
FIGS. 17A and 17B respectively depict a cross-sectional view and an assembly view of one exemplary embodiment of a shock-sensing and indicating device that comprises a two-component chemical reaction that results in a simple color change, chemi-luminescent output, or electro-chemical output when a shock of a certain level is sensed by a shock-sensing and indicating device according to the subject matter disclosed herein.
Figure 17B:
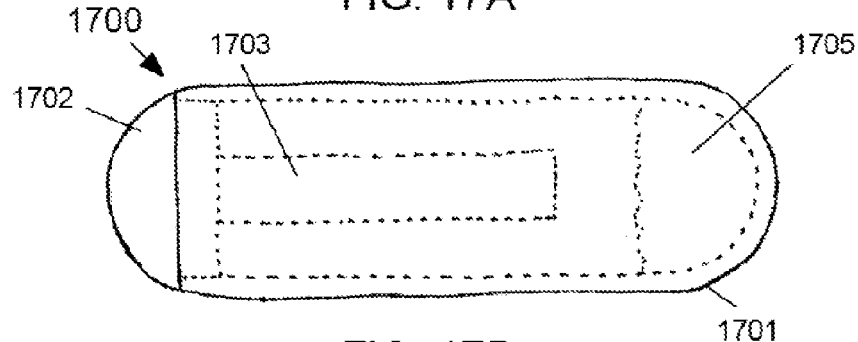

FIGS. 17A and 17B respectively depict a cross-sectional view and an assembly view of one exemplary embodiment of a shock-sensing and indicating device 1700 that comprises a two-component chemical reaction that results in a simple color change, chemi-luminescent output, or electrochemical output when a shock of a certain level is sensed by shock-sensing and indicating device 1700. Device 1700 comprises a main body 1701 and a reservoir/cap end 1702. Reservoir/cap end 1702 comprises a hollow-stem reservoir portion 1703 that contains a first component 1704. A wadding material 1705 impregnated with a second component 1706 is inserted into a reservoir 1707 formed internally to main body 1701. Reservoir/cap end 1702 is press fit into main body 1701 in a well-known manner. Main body 1701, reservoir/cap end 1702 and reservoir portion 1703 are formed from a clear or a translucent molded plastic, such as polycarbonate or copolyester. It should be understood that other suitable materials could be used to form main body 1701, reservoir/cap end 1702 and reservoir portion 1703. Wadding material 1705 comprises any wettable, hydrophilic fibrous material. In an exemplary alternative embodiment, the reservoir portion (portion 1703) could be formed as part of main body 1701. In yet another exemplary alternative embodiment, the reservoir portion could be a separate component that is, for example, press fit into either main body 1701 or cap end 1702. In yet another exemplary embodiment, the reservoir portion could comprise a plurality of reservoir tubes or portions. Different g-detection levels can be obtained through selection of materials used for the different components (body, reservoir and chemical components) of shock-sensing and indicating device 1700, and through selection of design dimensions and section contours of the main body and reservoir portions.

Figure 18A:
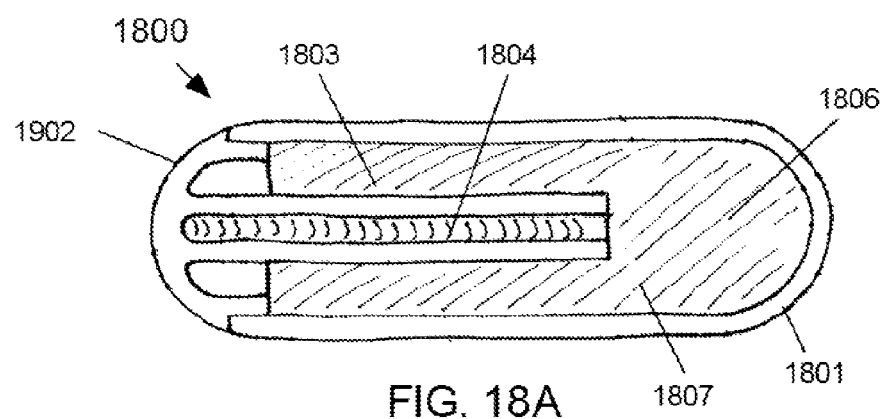
FIGS. 18A and 18B respectively depict a cross-sectional view and an assembly view of another exemplary embodiment of a shock-sensing and indicating device that comprises a two-component chemical reaction that results in a simple color change, chemi-luminescent output, or electrochemical output when a shock of a certain level is sensed by shock-sensing and indicating device according to the subject matter disclosed herein.
Figure 18B:
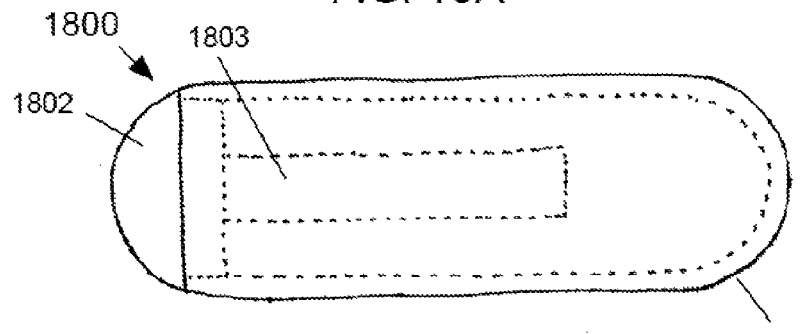

FIGS. 18A and 18B respectively depict a cross-sectional view and an assembly view of another exemplary embodiment of a shock-sensing and indicating device 1800 that comprises a two-component chemical reaction that results in a simple color change, chemi-luminescent output, or electrochemical output when a shock of a certain level is sensed by shock-sensing and indicating device 1800. Device 1800 comprises a main body 1801 and a reservoir/cap end 1802. Reservoir/cap end 1802 comprises a hollow-stem reservoir portion 1803 that contains a first component 1804. A second component 1806 is inserted into a reservoir 1807 formed internally to main body 1801. Reservoir/cap end 1802 is press fit into main body 1801 in a well-known manner. Main body 1801, reservoir/cap end 1802 and reservoir portion 1803 are formed from a clear or a translucent molded plastic, such as polycarbonate or copolyester. It should be understood that other suitable materials could be used to form main body 1801, reservoir/cap end 1802 and reservoir portion 1803. In an exemplary alternative embodiment, the reservoir portion (portion 1803) could be formed as part of main body 1801. In yet another exemplary alternative embodiment, the reservoir portion could be a separate component that is, for example, press fit into either main body 1801 or cap end 1802. In yet another exemplary embodiment, the reservoir portion could comprise a plurality of reservoir tubes or portions. Different g-detection levels can be obtained through selection of materials used for the different components (body, reservoir and chemical components) of shock-sensing and indicating device 1800, and through selection of design dimensions and section contours of the main body and reservoir portions.

Figure 19A:
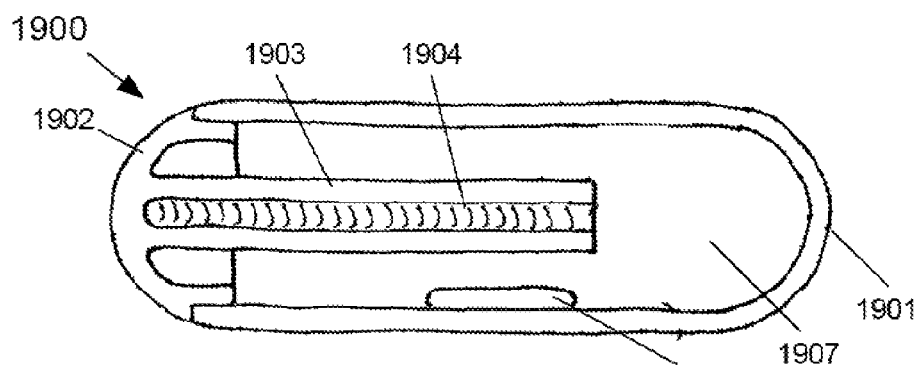
FIGS. 19A and 19B respectively depict a cross-sectional view and an assembly view of another exemplary embodiment of a shock-sensing and indicating device that comprises a two-component chemical reaction that results in a simple color change, chemi-luminescent output, or electrochemical output when a shock of a certain level is sensed by shock-sensing and indicating device according to the subject matter disclosed herein.
Figure 19B:
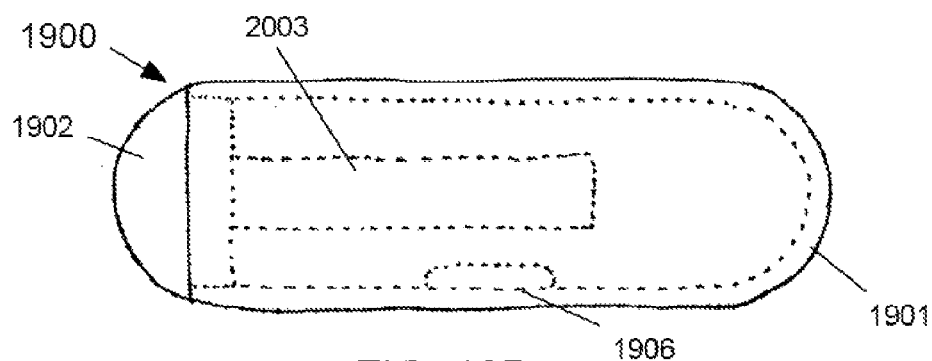

FIGS. 19A and 19B respectively depict a cross-sectional view and an assembly view of another exemplary embodiment of a shock-sensing and indicating device 1900 that comprises a two-component chemical reaction that results in a simple color change, chemi-luminescent output, or electrochemical output when a shock of a certain level is sensed by shock-sensing and indicating device 1900. Device 1900 comprises a main body 1901 and a reservoir/cap end 1902. Reservoir/cap end 1902 comprises a hollow-stem reservoir portion 1903 that contains a first component 1904. A second liquid component 1906 is inserted into a reservoir 1907 formed internally to main body 1901. Reservoir/cap end 1902 is press fit into main body 1901 in a well-known manner. Main body 1901, reservoir/cap end 1902 and reservoir portion 1903 are formed from a clear or a translucent molded plastic, such as polycarbonate or copolyester. It should be understood that other suitable materials could be used to form main body 1901, reservoir/cap end 1902 and reservoir portion 1903. In an alternative embodiment, the reservoir portion (portion 1903) could be formed as part of main body 1901. In yet another exemplary alternative embodiment, the reservoir portion could be a separate component that is, for example, press fit into either main body 1901 or cap end 1902. In yet another exemplary embodiment, the reservoir portion could comprise a plurality of reservoir tubes or portions. Different g-detection levels can be obtained through selection of materials used for the different components (body, reservoir and chemical components) of shock-sensing and indicating device 1900, and through selection of design dimensions and section contours of the main body and reservoir portions.

Figure 20A:
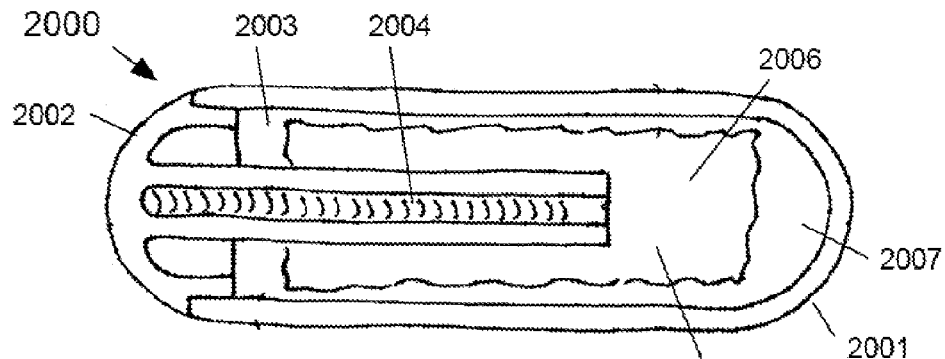
FIGS. 20A and 20B respectively depict a cross-sectional view and an assembly view of another exemplary embodiment of a shock-sensing and indicating device that comprises a two-component chemical reaction that results in a simple color change, chemi-luminescent output, or electrochemical output when a shock of a certain level is sensed by shock-sensing and indicating device according to the subject matter disclosed herein.
Figure 20B:
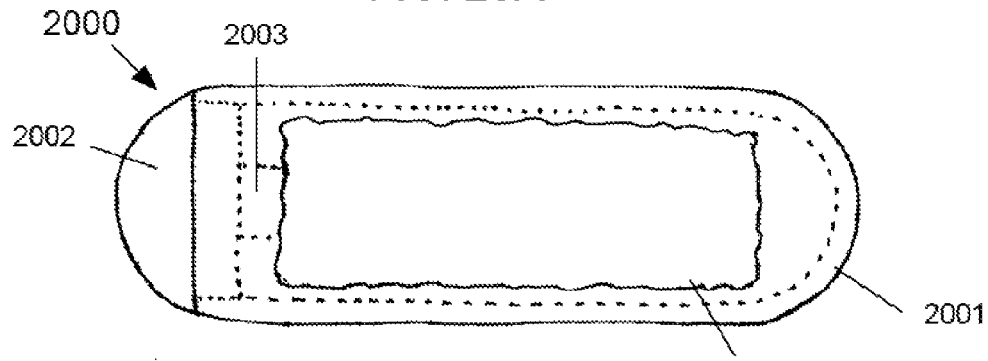

FIGS. 20A and 20B respectively depict a cross-sectional view and an assembly view of another exemplary embodiment of a shock-sensing and indicating device 2000 that comprises a two-component chemical reaction that results in a simple color change, chemi-luminescent output, or electrochemical output when a shock of a certain level is sensed by shock-sensing and indicating device 2000. Device 2000 comprises a main body 2001 and a reservoir/cap end 2002. Reservoir/cap end 2002 comprises a hollow-stem reservoir portion 2003 that contains a first component 2004. A media material 2005 impregnated with a second component 2006 is inserted into a reservoir 2007 formed internally to main body 2001. Reservoir/cap end 2002 is press fit into main body 2001 in a well-known manner. Main body 2001, reservoir/cap end 2002 and reservoir portion 2003 are formed from a clear or a translucent molded plastic, such as polycarbonate or copolyester. It should be understood that other suitable materials could be used to form main body 2001, reservoir/cap end 2002 and reservoir portion 2003. In an alternative embodiment, the reservoir portion (portion 2003) could be formed as part of main body 2001. In yet another exemplary alternative embodiment, the reservoir portion could be a separate component that is, for example, press fit into either main body 2001 or cap end 2002. In yet another exemplary embodiment, the reservoir portion could comprise a plurality of reservoir tubes or portions. Different g-detection levels can be obtained through selection of materials used for the different components (body, reservoir and chemical components) of shock-sensing and indicating device 2000, and through selection of design dimensions and section contours of the main body and reservoir portions.

Figure 21:
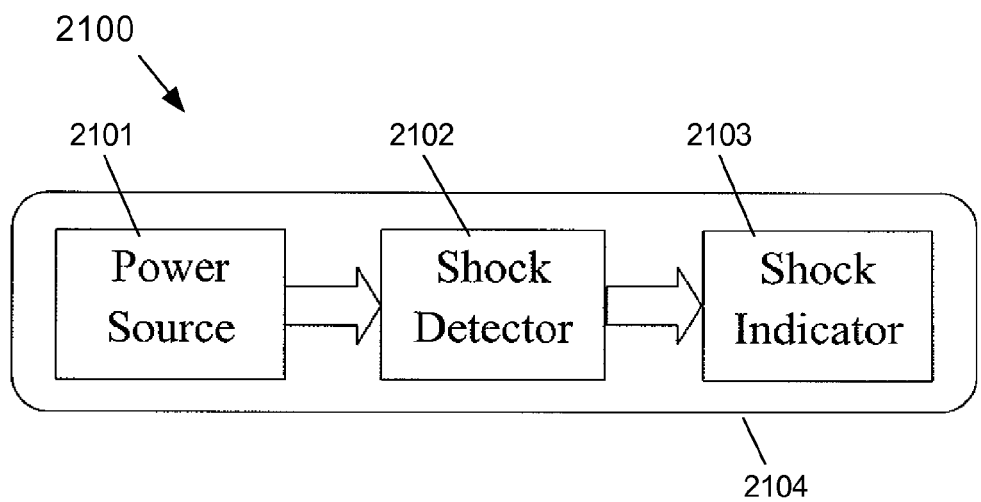
FIG. 21 depicts the three basic components for an exemplary embodiment of a shock-sensing and indicating system according to the subject matter disclosed herein.

One exemplary embodiment of a shock-sensing and indicating system that is suitable for use with, but not limited to, any of the exemplary embodiments disclosed herein includes three basic components. Other exemplary applications include, but are not limited to, shock-sensing and indicating for human and/or animal users for sporting events, military and tactical operations, aeronautical, and test- and space-flight operations, and industrial and vocational environments having a potential of exposure to high g forces or events. FIG. 21 depicts the three basic components for an exemplary embodiment of a shock-sensing and indicating system 2100. In particular, the three basic components include a power source 2101, such as a battery, piezoelectric device, Seebeck effect device, photovoltaic device, or coil and sliding magnet; a shock detector 2102, such as an accelerometer or strain gauge; and a shock-indicating device 2103, such as an indicating light, light emitting diode, dye projecting thermal drop-on-demand (DOD) inkjet, piezoelectric DOD inkjet, or electroluminescent device. Power source 2101 powers shock detector 2102. When shock detector 2102 senses a shock of a predetermined level, shock detector 2102 causes shock-indicating device 2103 to indicate that a shock of the predetermined level has been sensed. In one exemplary embodiment, the components forming shock-sensing and indicating system 2100 are contained within a suitable containing device 2104.

Figure 22:
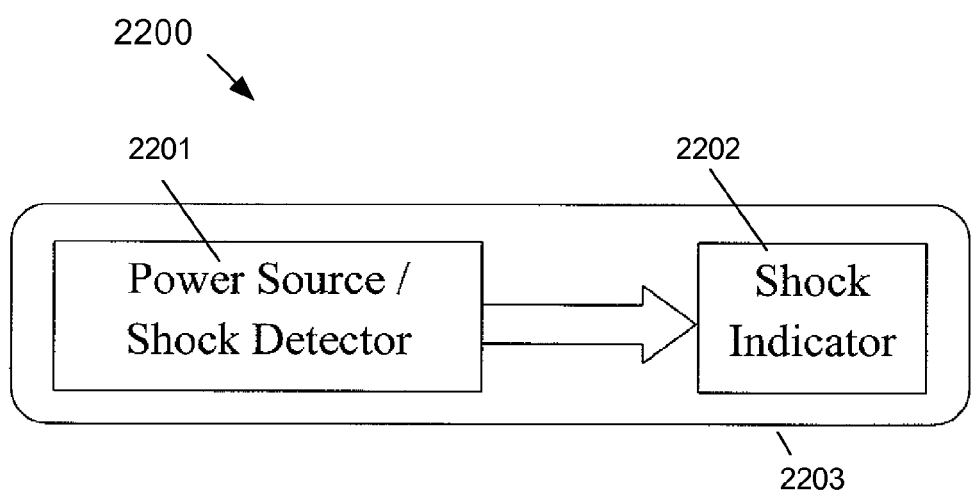
FIG. 22 depicts another exemplary embodiment of a shock detecting system according to the subject matter disclosed herein.

Another exemplary embodiment provides that a shock detection system, such as shown as system 2200 in FIG. 22, is inserted in or incorporated into an article of sporting equipment or apparel. Shock detection system 2100 comprises a power source/shock detector 2201, such as a piezoelectric device or a coil and sliding magnet, and a shock indicator device, 2202, such as an indicating light.

According to the subject matter disclosed herein, one or more active shock-sensing devices could be used in place of or in conjunction with the passive shock-sensing devices disclosed herein for the various exemplary embodiments of the subject matter disclosed herein. Suitable active shock-sensing devices include powered devices and non-powered shock-sensing devices.

One exemplary embodiment of an active shock-sensing device could comprise a non-powered piezoelectric sensor device configured to provide a piezoelectric voltage in response to a sensed shock that is sensed and recorded. In one exemplary embodiment, a piezoelectric sensor generates an electric potential in response to a strain on the piezoelectric sensor device causes by a shock applied to the sensor. In another exemplary embodiment, the voltage potential generated by the piezoelectric sensor device is used to trigger an electrochromic reaction that is visable and indicates that a shock greater than a predetermined magnitude has been experienced by the shock-sensing device. In another exemplary embodiment, the electric potential generated by the piezoelectric sensor device is sensed and recorded by, for example, to setting of an electronic register. For this exemplary embodiment, the shock-sensing device could be electronically scanned, such as by an RFID (RF Identification) device for determining whether the shock-sensing device has experienced a shock greater than a predetermined magnitude.

In another exemplary embodiment, such as a powered sensor having storage that can be queried by, for example, and RFID scanner. For this exemplary embodiment, the storage medium, such as an electronic register is powered and an electric potential provided by a piezoelectric sensor device when a shock is experienced is recorded in a well-known manner in the storage medium, by an electrical circuit that could then be queried using well-known RFID techniques to determine whether the shock-sensing device experienced a shock of a predetermined magnitude. Other powered shock-sensing devices could also be used, such as micro-accelerometers.

One exemplary embodiment comprises an active shock-sensing device that provides active continuous monitoring reporting of sensed shock by transmitting, for example, using an RFID-type communication technique, to a locally positioned receiver device that displays when a shock-sensor device experiences a predetermined level of shock. The shock-sensing and reporting capability could be continuous or could be recorded for later review. In one exemplary, the transmitter functionality provides sufficient range to transmit to a receiver that may be located, for example, on the sidelines of a football field.

Yet another exemplary embodiment comprises an Application Specific Integrated Circuit (ASIC) comprising microelectromechanical systems (MEMS) configured to sense, record and indicate shocks.

In one exemplary embodiment, energy for powering an active shock-sensing device comprises a Parametric Frequency Increased Generator (PFIGs), which is an energy-harvesting device that was developed by K. Najafi and T. Galchev at the University of Michigan Engineering Research Center for Wireless Integrated Microsystems. Such PFIGs are known to be highly efficient at providing renewable electrical power from arbitrary, non-periodic vibrations, such as the type of vibration that is a byproduct of humans when moving.

One exemplary embodiment of the subject matter disclosed herein comprises a shock-sensing unit comprising one or more passive and/or active shock-sensing devices that are attached to the chin strap of a helmet, such as a football helmet, the chin-strap cup of a chin strap of a helmet, the chin strap connection to a chin-strap cup. Still another exemplary embodiment provides that a shock-sensing unit be attached to a suitable surface of a helmet, such as, but not limited to, a football helmet, lacrosse helmet, or a motorcycle helmet.

One exemplary embodiment of the subject matter disclosed herein comprises a shock-sensing and indicating device that is subcutaneously or subdural inserted into a user for sensing and detecting shocks for indicating whether a user has experienced a level of shock in cranial and/or thoracic and abdominal regions of the user. For example, the subject matter disclosed herein is applicable for, but not limited to, shock-sensing and indicating for chest and cranial applications; applications in which high gs may be experienced by a user that are caused by explosions or crashes; applications in which a user may experience high levers of acceleration and/or deceleration, thereby indicating in situations in which the user is unconscious and that the user requires immediate critical medical attention.

Figure 23A:
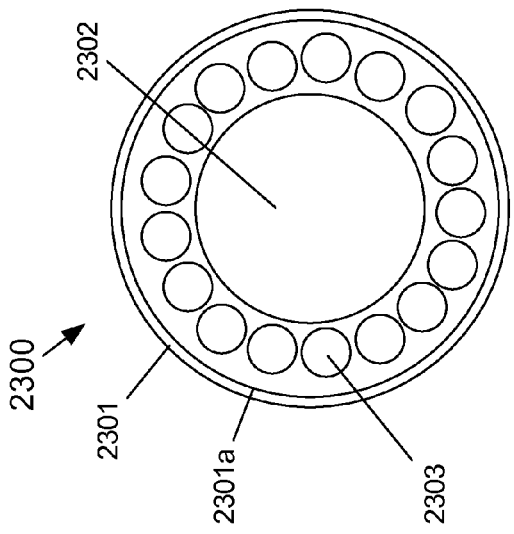
FIGS. 23A and 23B respectively depict a front and a sectional view of an exemplary embodiment of a two-axis, omni-directional shock-detection device according to the subject matter disclosed herein.
Figure 23B:
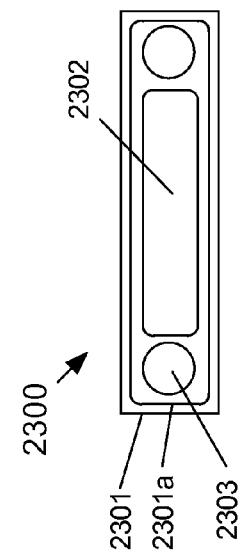

FIGS. 23A and 23B respectively depict a front and a sectional view of an exemplary embodiment of a two-axis, omni-directional shock-detection device 2300 according to the subject matter disclosed herein. The shock-detecting device 2300 depicted in FIGS. 23A and 23B comprises an assembly/housing 2301, a weighted striker device 2302, and a plurality of crushable reservoirs 2303, of which only one crushable reservoir is indicated in each of FIGS. 23A and 23B for clarity. Each crushable reservoir 2303 contains either a component A or a component B of a two-component chemical reaction system. In one exemplary embodiment, assembly/housing 2301 is formed from a transparent and/or translucent material, and contains weighted striker device 2302, the plurality of reservoirs 2303, which surround weighted striker device 2302 along an inside wall 2301a of assembly/housing 2301, and a component B, which fills substantially all remaining available space in assembly/housing 2301.

When shock-detecting device 2300 depicted in FIGS. 23A and 23B receives a shock or impact (i.e., assembly/housing 2301 is acted upon by an outside force), weighted striker device 2302 tends to stay in place until the force is transmitted through crushable reservoirs 2303 with sufficient force to move weighted striker device 2302. If the force is high enough, one or more crushable reservoirs 2303 will not be able to transmit the force without damage to itself, i.e., is crushed, and component A will be released into component B, thereby causing a chemical reaction or a state change of component B that provides an indication of the level of shock, such as, but not limited to, a change in conductivity of component B, a color change of component B, and/or a chemi-luminescent change of component B. In one exemplary embodiment, the indication provided by the mixing of components A and B is visible through assembly/housing 2301. Suitable materials for components A and B are described elsewhere herein. In another exemplary embodiment, a change in conductivity of component B can be detected and indicated using a Radio Frequency ID (RFID) device. In one exemplary embodiment, weighted striker device 2302 is textured to allow improved visibility and/or visual indication of a detected shock.

Figure 24:
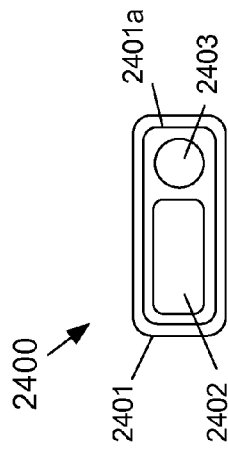
FIG. 24 depicts a sectional view of an exemplary embodiment of a one-axis, mono-directional shock-detecting device according to the subject matter disclosed herein.

FIG. 24 depicts a sectional view of an exemplary embodiment of a one-axis mono-directional shock-detecting device 2400 according to the subject matter disclosed herein. The exemplary embodiment of shock-detecting device 2400 depicted in FIG. 24 comprises an assembly/housing 2401, a weighted striker device 2402, and one or more crushable reservoirs 2403 that contain a component A, and a component B of a two-component chemical reaction system. In one exemplary embodiment, assembly/housing 2401 is formed from a transparent and/or translucent material, and contains weighted striker device 2402, the plurality of reservoirs 2403, which are positioned between weighted striker device 2402 and an inside wall 2401a of assembly/housing 2401, and the component B, which fills substantially all remaining available space in assembly/housing 2401. In another exemplary embodiment, each reservoir 2403 contains either a component A or a component B. Crushable reservoirs 2403 are positioned within assembly housing 2401 along one side of weighted striker device 2402 between weighted striker device 2402 and an inside wall 2401a.

When shock-detecting device 2400 depicted in FIG. 24 receives a shock or impact (i.e., assembly/housing 2401 is acted upon by an outside force), weighted striker device 2402 tends to stay in place until the force is transmitted through crushable reservoirs 2403 with sufficient force to move weighted striker device 2402. If the force is high enough, one or more crushable reservoirs 2403 will not be able to transmit the force without damage to itself, i.e., is crushed, and component A will be released into component B, thereby causing a chemical reaction or a state change of component B that provides an indication of the level of shock, such as, but not limited to, a change in conductivity of component B, a color change of component B, and/or a chemi-luminescent change of component B. In one exemplary embodiment, the indication provided by the mixing of components A and B is visible through assembly/housing 2401. Suitable materials for components A and B are described elsewhere herein. In another exemplary embodiment, a change in conductivity of component B can be detected and indicated using a Radio Frequency ID (RFID) device. In use, the one-axis mono-directional shock-detecting device 2400 depicted in FIG. 24 can be oriented along an axis that a shock is desired to be detected.

Figure 25:
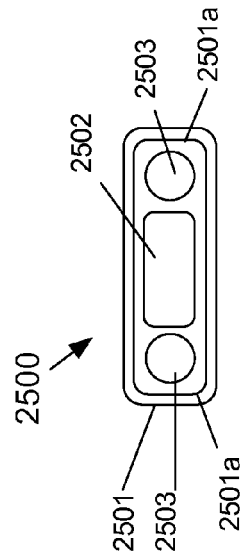
FIG. 25 depicts a sectional view of an exemplary embodiment of a one-axis, bi-directional shock-detecting device according to the subject matter disclosed herein.

FIG. 25 depicts a sectional view of an exemplary embodiment of a one-axis bi-directional shock-detecting device 2500 according to the subject matter disclosed herein. The exemplary embodiment of shock-detecting device 2500 depicted in FIG. 25 comprises an assembly/housing 2500, a weighted striker device 2502, and one or more crushable reservoirs 2503 that contain a component A, and a component B of a two-component chemical reaction system. In one exemplary embodiment, assembly/housing 2501 is formed from a transparent and/or translucent material, and contains weighted striker device 2502, the plurality of reservoirs 2503, which are positioned on opposite sides of weighted striker device 2502 between an inside wall 2501a of assembly/housing 2501 and striker device 2502. Component B fills substantially all remaining available space in assembly/housing 2501. In another exemplary embodiment, each reservoir 2503 contains either a component A or a component B. Crushable reservoirs 2503 are positioned within assembly/housing 2503 along opposite sides of weighted striker device 2502. In one exemplary embodiment, crushable reservoirs 2503 are positioned within assembly/housing 2501 with respect to weighted striker device 2502 along axes in which shock is desired to be detected.

Figure 26A:
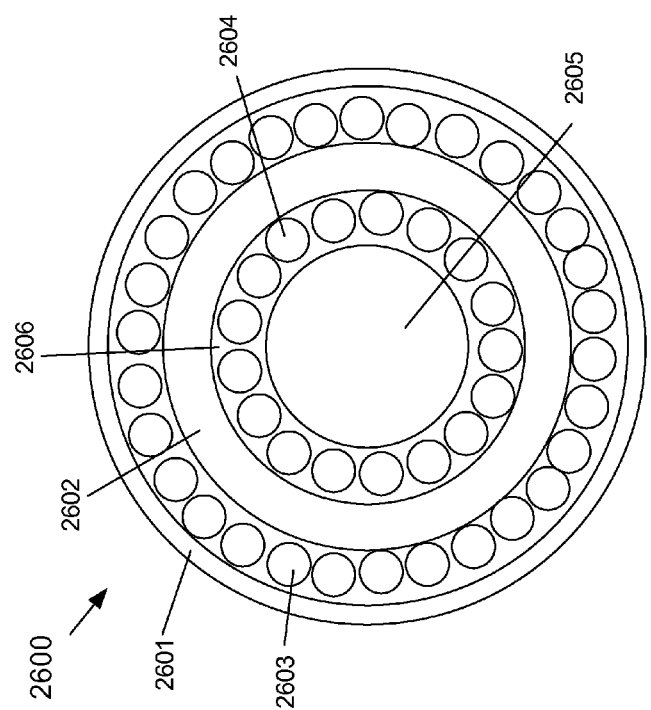
FIGS. 26A and 26B respectively depict a front and a sectional view of another exemplary embodiment of a two-axis, omni-directional shock-detection device according to the subject matter disclosed herein.
Figure 26B:
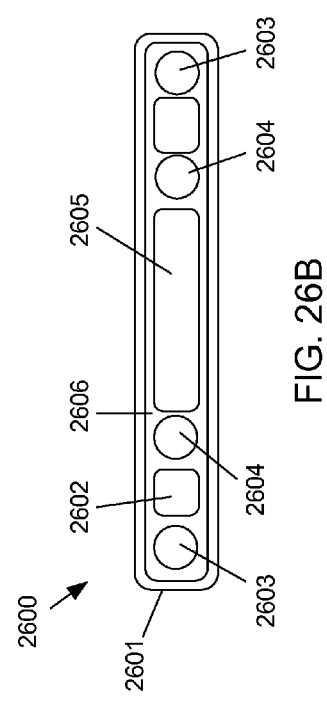

When the shock-detecting device 2500 depicted in FIG. 25 receives a shock or impact (i.e., assembly/housing is acted upon by an outside force), weighted striker device 2502 tends to stay in place until the force is transmitted through crushable reservoirs 2503 with sufficient force to move weighted striker device 2503. If the force is high enough, one or more crushable reservoirs 2503 will not be able to transmit the force without damage to itself, i.e., is crushed, and component A will be released into component B, thereby causing a chemical reaction or a state change of component B that provides an indication of the level of shock, such as, but not limited to, a change in conductivity of component B, a color change of component B, and/or a chemi-luminescent change of component B. In one exemplary embodiment, the indication provided by the mixing of components A and B is visible through the assembly/housing. Suitable materials for components A and B are disclosed by, but are not limited to, U.S. Provisional Patent Application Ser. No. 61/309,818, U.S. Provisional Patent Application Ser. No. 61/320,724, and U.S. Non-Provisional patent application Ser. No. 12/831,860, the disclosures of which have been incorporated by reference herein. In another exemplary embodiment, a change in conductivity of component B can be detected and indicated using a Radio Frequency ID (RFID) device. FIGS. 26A and 26B respectively depict a front and a sectional view of another exemplary embodiment of a two-axis, omni-directional shock-detection device 2600 according to the subject matter disclosed herein. The shock-detecting device 2600 depicted in FIGS. 26A and 26B comprises an assembly/housing 2601, an outer weighted striker device 2602, and a plurality of crushable reservoirs 2603 that contain a component A, a component B, a plurality of crushable reservoirs 2604 that contain a component C, and an inner weighted striker device 2605. In another exemplary embodiment, each reservoir 2603 and 2604 contains a component A, a component B or a component C of a multi-component chemical reaction system. In one exemplary embodiment, the assembly/housing 2601 is formed from a transparent and/or translucent material, and contains weighted striker devices 2602 and 2605, the plurality of reservoirs 2603 and 2604, which surround weighted striker devices 2602 and 2605, and the component B, which fills substantially all remaining available space in the assembly/housing 2601. Outer weighted striker device 2602 is configured to include an inner cavity or space 2606 that contains the plurality of crushable reservoirs 2604 that contain component C and inner weighted striker device 2605. Assembly/housing 2601 is formed from a transparent and/or translucent material so that it is visible when the shock-detecting device senses a shock as described below.

In one exemplary embodiment, component A and component C are the same and provide the same type of visual indication when shock-detecting device 2600 senses a shock. In another exemplary embodiment, component A and component C are different, but both provide a different visual indication when the shock-detecting device 2600 senses a shock. In another exemplary embodiment, the crushable reservoirs that contain component A are similar to the crushable reservoirs that contain component C in that both reservoirs crush in response to substantially the same force. In yet another exemplary embodiment, the crushable reservoirs that contain component A are different to the crushable reservoirs that contain component C in that the respective reservoirs crush in response to substantially different forces. In still other exemplary embodiments, the respective weights of the outer and inner weighted striker devices can be selected so that they can be the same or be different.

When the shock-detecting device 2600 depicted in FIGS. 26A and 26B receives a shock or impact (i.e., assembly/housing 2601 is acted upon by an outside force), outer weighted striker device 2602 tends to stay in place until the force is transmitted through the crushable reservoirs 2603 (containing component A) with sufficient force to move outer weighted striker device 2602. If the force is high enough, one or more crushable reservoirs 2603 (containing component A) will not be able to transmit the force without damage to itself (i.e., being crushed), and component A will be released into component B, thereby causing a chemical reaction or a state change of component B that provides an indication of the level of shock, such as, but not limited to, a change in conductivity of component B, a color change of component B, and/or a chemi-luminescent change of component B. Similarly, when outer weighted striker device 2602 moves, inner weighted striker device 2605 tends to stay in place until the force is transmitted through the crushable reservoirs 2604 (containing component C) with sufficient force to move inner weighted striker device 2605. If the force is high enough, one or more crushable reservoirs 2604 (containing component C) will not be able to transmit the force without damage to itself (i.e., is crushed), and component C will be released into component B, thereby causing a chemical reaction or a state change of component B that provides an indication of the level of shock, such as, but not limited to, a change in conductivity of component B, a color change of component B, and/or a chemi-luminescent change of component B.

In one exemplary embodiment, the indication provided by the mixing of components A, B and C is visible through assembly/housing 2601. Suitable materials for components A and B are described elsewhere herein. In another exemplary embodiment, a change in conductivity of component B can be detected and indicated using a Radio Frequency ID (RFID) device.

In another exemplary embodiment of the subject matter disclosed herein, the exemplary embodiments of the shock-detecting device depicted in FIGS. 23-26 could comprise an assembly/housing, a weighted striker device and a photonic crystal material having a physical structure or chemical solution that changes optical properties when exposed to a force that destroys at least a portion of the lattice structure of the photonic crystal material. The photonic crystal material has certain optical properties that are based on the lattice structure of the material. The term "optical properties," as used herein, may include one or more wavelengths within the electromagnetic spectrum transmitted or reflected by the material (for example, a wavelength of 530 nm corresponds to green light within the visible spectrum), a color profile across the material, a color or absence of color, luminance, radiance, brightness, or any other visual property observable or measurable on the material. Additionally, the term "color profile," as used herein, is intended to mean the range of particular colors exhibited by the material across its surface and the effect on the viewed color at the various regions of the material. The color profile may change as a function of a viewing angle, described further below. Luminance may be defined as an indicator of how bright the material appears and may be measured in candela per square meter ($cd/m^2$). Further, radiance may be an indicator of how bright the material appears and may be measured in watts per steradian per square meter ($W/sr \cdot m^2$). It is recognized that any suitable visual or measurable technique may be used to determine optical properties of the material.

Suitable photonic crystal materials may comprise, but are not limited to, a polymer, such as a negative-tone photoresist polymer. In one exemplary embodiment, Epon SU-8, a commercially available negative-tone photoresist based on a multifunctional glycidyl ether derivative of bisphenol-A novolac epoxy resin may be used. Other materials of interest may include, but are not limited to, suitable materials in the categories of thermoplastics, elastomers, and thermoelastomers, such as polystyrene, methacrylates, acrylates, polyimide, polyurethane, epoxy and silicones chosen by one skilled in the art. It is understood that any suitable polymer capable of being formed into a photonic crystal material may be used. The use of the SU-8 photoresist ensures that the photonic crystal material is thermochemically stable. Accordingly, the material may be durable even under extreme motion, moisture, and temperature parameters, which often occur in combat situations. Specifically, exposed SU-8 resist is thermally stable (up to 300° C.) and chemically stable due to its aromatic functionality and high cross-link density. Additional details regarding suitable photonic crystal materials are disclosed by U.S. Published Patent Application Serial No. 2010/0073678 A1 to Smith et al., the disclosure of which is incorporated by reference herein. The shock-detecting device of this exemplary embodiment is configured similarly to, but not limited to, the exemplary embodiments of FIGS. 23-26 with the photonic crystal material surrounding the weighed striker device within the assembly/housing. In one exemplary embodiment, the photonic crystal material is selectively positioned on one or more sides of the weighted striker device within the assembly/housing to detect a shock along one or more selected axes.

When the shock-detecting device of this exemplary embedment receives a shock or impact (i.e., assembly/housing is acted upon by an outside force), the weighted striker device tends to stay in place until the force is transmitted through the photonic crystal material with sufficient force to move the weighted striker device. If the force is high enough, the photonic crystal material will not be able to transmit the force without damage to it, i.e., will be crushed, and thereby destroying at least a portion of the lattice structure of the photonic crystal material.

It should be understood that the shapes of the various objects depicted in FIGS. 23-26 are not limited to the shapes shown. Additionally, while relatively large crushable reservoirs are depicted, relatively smaller crushable reservoirs could alternatively be used. Further, while the exemplary embodiments depicted in FIGS. 23-26 generally detect a shock along one or more planar axes, one or more exemplary embodiments of the subject matter disclosed herein could comprise crushable reservoirs and/or a photonic crystal material that completely surrounds a weighted striker device for omni-directional shock sensing (i.e., three directions). Additionally, the weight of the weighted striker device can be selected so that the shock-detecting device detects and indicates a shock at a particular level of shock. In one exemplary embodiment, a plurality of shock-detecting devices according to the subject matter disclosed herein each having different selected weights for the weighted striker device can be used together to detect and indicate a range of shocks.

It should be understood that the two-weighted striker device concept can be applied to the exemplary embodiments depicted in FIGS. 24 and 25. That is, two striker devices, each having selectably different weights, and two sets of crushable reservoirs could be used for detecting and indicating different levels of shock received by a shock-detecting device according to the subject matter disclosed herein. Moreover, it should be understood that a shock-detecting device could be configured to comprise more than two weighted striker devices and thereby detect and indicate a number of different levels of shock received by a shock-detecting device according to the subject matter disclosed herein. In one exemplary embodiment, a shock level received by a shock-detecting device according to the subject matter disclosed herein could comprise a weighted striker device having factory aligned pins, or contacts, that is immersed in a viscous, non-conductive media. When the shock-detecting device receives a shock or impact (i.e., assembly/housing is acted upon by an outside force), the weighted striker device contained in the housing/assembly tends to stay in place until the force is transmitted through the viscous media with sufficient force to deform or move the pins, or contact, on the weighted striker device, thereby making contact with each other and forming an electrical circuit. In another exemplary embodiment, factory aligned pins, or contacts, could be positioned on the inside surface of the housing/assembly, in which case the detecting circuit would be formed as part of the housing/assembly. In yet another exemplary embodiment, the pins, or terminals, could be selected so that different levels of force are needed to deform different pairs of pins, thereby sensing different levels of shock depending on the particular pins that have been deformed to complete an electrical circuit.

In another exemplary embodiment, a shock-detecting device comprises a housing/assembly containing a cavity comprising a viscous medium in which a plurality of pin-like elements is suspended in the viscous medium. The pin-like elements are configured to have one end that is heavier than the other end, such as by being a "ball" end. When assembled, the pin-like elements have a generally random arrangement was they are suspended in the viscous medium. The viscosity and the weights of the pin-like elements are selected so that when the shock-detecting device receives a shock, the "ball" ends of the pin-like elements tend to align, thereby indicating a level of shock received by the shock-detecting device. In another exemplary embodiment, the pin-like elements, when assembled in the housing/assembly, are generally aligned. The viscosity and the weights of the pin-like elements are selected so that when the shock-detecting device receives a shock, the "ball" ends of the pin-like elements tend to randomized, thereby indicating a visual level of shock received by the shock-detecting device. In another exemplary embodiment, the pin-like elements are conductive, when assembled in the housing/assembly, are generally aligned so that the pin-like elements are collectively non-conductive. The viscosity and the weights of the pin-like elements are selected so that when the shock-detecting device receives a shock, the "ball" ends of the pin-like elements tend to randomized so that the pin-like elements collectively become more conductive, thereby indicating with the level of collective conductivity of the pin-like elements a level of shock received by the shock-detecting device.

Figure 27:
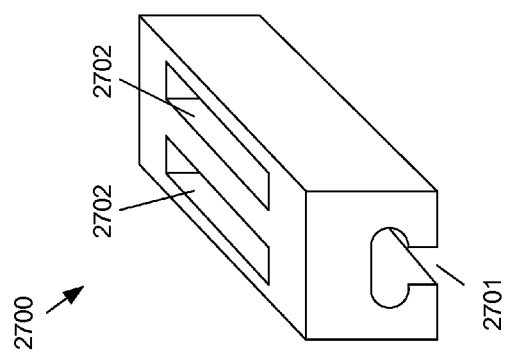
FIG. 27 depicts an alternative exemplary non-limiting embodiment of a shock-sensing device adaptor that can be coupled to a mouth guard strap according to the subject matter disclosed herein.

FIG. 27 depicts an alternative exemplary non-limiting embodiment of a shock-sensing device adaptor 2700 that can be coupled to a mouth guard strap according to the subject matter disclosed herein. More particularly, the exemplary shock-sensing device adaptor 2700 depicted in FIG. 27 is capable of being coupled to a strap (not shown) of a mouth guard that attaches the mouth guard to, for example, the facemask of a football helmet. In FIG. 27, shock-sensing device adaptor 2700 comprises an aperture 2701 that receives the mouth-guard strap the mouth guard. Any of the exemplary embodiments of a shock-detecting device disclosed herein is received by an aperture 2702. Each aperture 2702 is configured to receive the specific embodiment of the shock-detecting device. In one exemplary embodiment, the shock-detecting devices are replaceable. In another exemplary embodiment, the shock-detecting devices are not replaceable because apertures 2702 are sealed after the shock-detecting devices are inserted. FIGS. 28-31 depict alternative exemplary embodiments of a shock-sensing device that can be mounted into a strap hole of a mouth guard according to the subject matter disclosed herein. FIGS. 28A and 28B respectively depict front and side views of an exemplary non-limiting embodiment of a shock-sensing device 2800 that can be mounted into a hole on a mouth guard. The hole could be an existing hole on an existing mouth guard, such as a strap hole, or could be a hole that is specially fabricated for the subject matter disclosed herein. FIG. 28C depicts a side view of a non-limiting exemplary embodiment 2800 comprising a single post bottom 2801. FIG. 28D depicts a side view of a non-limiting exemplary embodiment comprising two post bottoms 2801. While the shock-sensing elements depicted in FIGS. 28A-28D represent spill-type-technology shock-sensing devices, the shock-sensing elements could alternatively be any of the different shock-sensing elements and/or devices disclosed herein.

FIGS. 29A and 29B respectively depict front and side views of another exemplary non-limiting embodiment of a shock-sensing device 2900 that can be mounted into a hole on a mouth guard. The hole could be an existing hole on an existing mouth guard, such as a strap hole, or could be a hole that is specially fabricated for the subject matter disclosed herein. FIG. 29B, in particular, depicts a side view of a non-limiting exemplary embodiment 2900 comprising a single post bottom 2901. FIG. 29C depicts a side view of a non-limiting exemplary embodiment comprising two post bottoms 2901. While the shock-sensing elements depicted in FIGS. 29A-29C represent crush-type-technology shock-sensing devices, the shock-sensing elements could alternatively be any of the different shock-sensing elements and/or devices disclosed herein.

FIGS. 30A and 30B respectively depict front and side views of yet another exemplary non-limiting embodiment of a shock-sensing device 3000 that can be mounted into a hole on a mouth guard. The hole could be an existing hole on an existing mouth guard, such as a strap hole, or could be a hole that is specially fabricated for the subject matter disclosed herein. FIG. 30C, in particular, depicts a side view of a non-limiting exemplary embodiment 3000 comprising a single post bottom 3001. FIG. 30D depicts a side view of a non-limiting exemplary embodiment 3000 comprising two post bottoms 3001. While the shock-sensing elements depicted in FIGS. 30A-30D represent crush-type-technology shock-sensing devices, the shock-sensing elements could alternatively be any of the different shock-sensing elements and/or devices disclosed herein.

FIGS. 31A-31C respectively depict front, side and bottom views of an exemplary non-limiting embodiment of a shock-sensing device 3100 that can be mounted to the strap of a mouth guard. FIG. 31D depicts a side view of a non-limiting exemplary embodiment of a strap 3110 that has been modified to receive the exemplary device of FIGS. 31A-31C. FIG. 31E depicts a shock-sensing device mounted on the strap of a mouth guard. While the shock-sensing elements depicted in FIGS. 31A-31C represent spill-type-technology shock-sensing devices, the shock-sensing elements could alternatively be any of the different shock-sensing elements and/or devices disclosed herein.

Although the foregoing disclosed subject matter has been described in some detail for purposes of clarity of understanding, it will be apparent that certain changes and modifications may be practiced that are within the scope of the appended claims. Accordingly, the present embodiments are to be considered as illustrative and not restrictive, and the subject matter disclosed herein is not to be limited to the details given herein, but may be modified within the scope and equivalents of the appended claims.

What is claimed is:

1. A mouth guard, comprising:
   a base member configured to fit inside a mouth of a user;
   at least one shock-sensing device directly attached to the base member, the at least one shock-sensing device to detect a level of shock applied to the base member that exceeds a predetermined level of shock; and
   an indicating device directly attached to the base member and coupled to the at one shock-sensing device to indicate that the shock-sensing device has detected a level of shock that has been applied to the base member that exceeds the predetermined level of shock, the indicating device comprising a light or a light emitting diode.

2. The mouth guard according to claim 1, wherein the at least one shock-sensing and indicating device detects a shock substantially along a selected axis with respect to the base member.

3. The mouth guard according to claim 1, wherein the at least one shock-sensing and indicating device detects a shock substantially along a plurality of selected axes with respect to the base member, each selected axis being substantially orthogonal from another selected axis.

4. The mouth guard according to claim 1, wherein the at least one shock-sensing device comprises at least one accelerometer to detect a level of shock applied to the base member that exceeds a predetermined shock level.

* * * * *